US009872868B2

(12) United States Patent
Morrison et al.

(10) Patent No.: US 9,872,868 B2
(45) Date of Patent: Jan. 23, 2018

(54) MITOCHONDRIALLY-TARGETED ELECTROPHILIC COMPOUNDS AND METHODS OF USE FOR THE TREATMENT OF CANCER

(71) Applicant: UAB Research Foundation, Birmingham, AL (US)

(72) Inventors: Aimee Morrison, Trussville, AL (US); Sadanandan Velu, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 14/911,703

(22) PCT Filed: Aug. 15, 2014

(86) PCT No.: PCT/US2014/051372
§ 371 (c)(1),
(2) Date: Feb. 11, 2016

(87) PCT Pub. No.: WO2015/024000
PCT Pub. Date: Feb. 19, 2015

(65) Prior Publication Data
US 2016/0193235 A1 Jul. 7, 2016

Related U.S. Application Data

(60) Provisional application No. 61/866,418, filed on Aug. 15, 2013.

(51) Int. Cl.
*A61K 31/095* (2006.01)
*A61K 31/14* (2006.01)
*A61K 31/66* (2006.01)
*A61K 51/04* (2006.01)
*A61K 45/06* (2006.01)
*C07F 9/54* (2006.01)

(52) U.S. Cl.
CPC ............ *A61K 31/66* (2013.01); *A61K 31/095* (2013.01); *A61K 31/14* (2013.01); *A61K 45/06* (2013.01); *A61K 51/04* (2013.01); *A61K 51/0497* (2013.01); *C07F 9/5442* (2013.01)

(58) Field of Classification Search
CPC ....... A61K 31/095; A61K 31/14; A61K 31/66
See application file for complete search history.

(56) References Cited

U.S. PATENT DOCUMENTS

| 8,466,140 B2 | 6/2013 | Altieri et al. |
| 2013/0064768 A1 | 3/2013 | Menon et al. |

FOREIGN PATENT DOCUMENTS

WO   WO 2012/103455   8/2012

OTHER PUBLICATIONS

Andringa et al. "Analysis of the liver mitochondrial proteome in response to ethanol and S-adenosylmethionine treatments: novel molecular targets of disease and hepatoprotection" *The American Journal of Physiology—Gastrointestinal and Liver Physiology* 298:G732-G745 (2010).
Bailey et al. "Mitochondrial proteomics in free radical research" *Free Radical Biology & Medicine* 38(2):175-188 (2005) (Abstract only).
Bailey et al. "S-adenosylmethionine prevents chronic alcohol-induced mitochondrial dysfunction in the rat liver" *The American Journal of Physiology—Gastrointestinal and Liver Physiology* 291:G857-G867 (2006).
Bailey et al. "Proteomic Approaches to Identify and Characterize Alterations to the Mitochondrial Proteome in Alcoholic Liver Disease" *Methods in Molecular Biology* 447:369-380 (2008).
Chambers et al. "Dissemination and Growth of Cancer Cells in Metastatic Sites" *Nature Reviews Cancer* 2:563-572 (2002).
Charles et al. "Redox regulation of soluble epoxide hydrolase by 15-deoxy-Δ—prostaglandin $J_2$ controls coronary hypoxic vasodilation" *Circulation Research* 108(3):324-334 (2011).
Diers et al. "Modulation of mammary cancer cell migration by 15-deoxy-$\Delta^{12,14}$—prostaglandin $J_2$: implications for anti-metastatic therapy" *Biochemical Journal* 430(1):69-78 (2010).
Diers et al. "Mitochondrial targeting of the electrophilic lipid 15-deoxy-$\Delta^{12,14}$-Prostaglandin $J_2$ increases apoptotic efficacy via redox cell signaling mechanisms" *Biochemical Journal* 426(1):31-41 (2011).
Diers et al. "Mitochondrial Bioenergetics of Metastatic Breast Cancer Cells in Response to Dynamic Changes in Oxygen Tension: Effects of HIF-1α" *PLoS One* 8(6):e68348 (2013).
Dranka et al. "Assessing bioenergetic function in response to oxidative stress by metabolic profiling" *Free Radical Biology & Medicine* 51(9):1621-1635 (2011).
Fenster et al. "Weight loss and race modulate nitric oxide metabolism in overweight women" *Free Radical Biology & Medicine* 37(5):695-702 (2004) (Abstract only).
Gane et al. "The mitochondria-targeted anti-oxidant mitoquinone decreases liver damage in a phase II study of hepatitis C patients" *Liver International* 30:1019-1026 (2010).
Higdon et al. "Methods for imaging and detecting modification of proteins by reactive lipid species" *Free Radical Biology & Medicine* 47(3):201-212 (2009).
Higdon et at "Cell signalling by reactive lipid species: new concepts and molecular mechanisms" *Biochemical Journal* 442:453-464 (2012).
Hill et al. "Methods for the determination and quantification of the reactive thiol proteome" *Free Radical Biology & Medicine* 47(6):675-683 (2009).
Kleinman et al. "Invasion assays" *Current Protocols in Cell Biology* Chapter 12: Unit 12.2 (2001) (Abstract only).
Landar et al. "A sensitive method for the quantitative measurement of protein thiol modification in response to oxidative stress" *Free Radical Biology & Medicine* 40(3):459-468 (2006) (Abstract only).
Landar et al. "Induction of the permeability transition and cytochrome c release by 15-deoxy-$\Delta^{12,14}$-prostaglandin $J_2$ in mitochondria" *Biochemical Journal* 394:185-195 (2006).

(Continued)

*Primary Examiner* — Yong Chong
(74) *Attorney, Agent, or Firm* — Myers Bigel, P.A.

(57) ABSTRACT

The present invention provides methods, compounds, compositions and kits including mitochondrially-targeted electrophilic (MTE) compounds that are useful for treating cancer.

7 Claims, 9 Drawing Sheets

(56) References Cited

OTHER PUBLICATIONS

Li et al. "A $^{99m}$Tc-Labeled Triphenylphosphonium Derivative for the Early Detection of Breast Tumors" *Cancer Biotherapy and Radiopharmaceuticals* 24(5):579-587 (2009).

Lin et al. "Specific Modification of Mitochondrial Protein Thiols in Response to Oxidative Stress: a Proteomics Approach" *The Journal of Biological Chemistry* 277(19):17048-17056 (2002).

Londono-Joshi et al. "Basal-like breast cancer stem cells are sensitive to anti-DR5 mediated cytotoxicity" *Breast Cancer Research & Treatment* 133(2):437-445 (2012).

Marley et al. "Mass tagging approach for mitochondrial thiol proteins" *Journal of Proteome Research* 4(4):1403-1412 (2005) (Abstract only).

McGonigle et al. "In vitro assay of angiogenesis: inhibition of capillary tube formation" *Current Protocols in Pharmacology* Chapter 12:Unit 12.12 (2008) (Abstract only).

Murphy, Michael P. "Targeting lipophilic cations to mitochondria" *Biochimica et Biophysica Acta* 1777:1028-1031 (2008).

Oh et al. "Methods for Determining the Modification of Protein Thiols by Reactive Lipids" *Methods in Cell Biology* 80:417-434 (2007) (Abstract only).

Oh et al. "Accumulation of 15- deoxy-$\Delta^{12,14}$-prostaglandin J$_2$ adduct formation with Keap1 over time: effects on potency for intracellular antioxidant defence induction" *Biochemical Journal* 411(2):297-306 (2008).

Oliva et al. "Acquisition of Temozolomide Chemoresistance in Gliomas Leads to Remodeling of Mitochondrial Electron Transport Chain" *The Journal of Biological Chemistry* 285(51):39759-39767 (2010).

Oliver et al. "Effect of anti-DR5 and chemotherapy on basal-like breast cancer" *Breast Cancer Research & Treatment* 133(2):417-426 (2012).

Ricart et al. "The permissive role of mitochondria in the induction of haem oxygenase-1 in endothelial cells" *Biochemical Journal* 419(2):427-436 (2009).

Ross et al. "Accumulation of lipophilic dications by mitochondria and cells" *Biochemical Journal* 400:199-208 (2006).

Ross et al. "Rapid and extensive uptake and activation of hydrophobic triphenylphosphoniunn cations within cells" *Biochemical Journal* 411:633-645 (2008).

Smith et al. "Delivery of bioactive molecules to mitochondria in vivo" *Proceedings of the National Academy of Sciences* 100(9):5407-5412 (2003).

Smith et al. "Animal and human studies with the mitochondria-targeted antioxidant MitoQ" *Annals of the New York Academy of Sciences* 1201:96-103 (2010).

Smith et al. "Mitochondria-Targeted Small Molecule Therapeutics and Probes" *Antiocidants & Redox Signaling* 15(12):3021-3038 (2011).

Smith et al. "Mitochondria-targeted antioxidants as therapies" *Discovery Medicine* 11(57):106-114 (2011) (Abstract only).

Snow et al. "A Double-Blind, Placebo-Controlled Study to Assess the Mitochondria-Targeted Antioxidant MitoQ as a Disease-Modifying Therapy in Parkinson's Disease" *Movement Disorders* 25(11):1670-1674 (2010).

Steeg, Patricia S. "Tumor metastasis: mechanistic insights and clinical challenges" *Nature Medicine* 12(8):895-904 (2006).

Venkatraman et al. "Modification of the Mitochondrial Proteome in Response to the Stress of Ethanol-dependent Hepatotoxicity" *The Journal of Biological Chemistry* 279(21):22092-22101 (2004).

Venkatraman et al. "Oxidative modification of hepatic mitochondria protein thiols: effect of chronic alcohol consumption" *The American Journal of Physiology—Gastrointestinal and Liver Physiology* 286:G521-G527 (2004).

Wall et al. "Oxidative modification of proteins: an emerging mechanism of cell signaling" *Frontiers in Physiology* 3(369):1-9 (2012).

Zelickson et al. "Nitric oxide and hypoxia exacerbate alcohol-induced mitochondrial dysfunction in hepatocytes" *Biochimica et Biophysica Acta* 1807(12):1573-1582 (2011).

Notification Concerning Transmittal of International Preliminary Report on Patentability corresponding to International Application No. PCT/US2014/051372 dated Feb. 25, 2016.

Notification of Transmittal of the International Search Report and the Written Opinion, of the International Searching Authority, or the Declaration corresponding to International Application No. PCT/US2014/051372 dated Nov. 13, 2014.

MITOCHONDRIALLY-TARGETED ELECTROPHILIC COMPOUNDS AND METHODS OF USE FOR THE TREATMENT OF CANCER

STATEMENT OF PRIORITY

This application is a 35 U.S.C. § 371 of national phase application of PCT Application No. PCT/US2014/051372, filed Aug. 15, 2014, which claims the benefit, under 35 U.S.C. § 119(e), of U.S. Provisional Application Ser. No. 61/866,418, filed Aug. 15, 2013, the entire contents of each of which are incorporated by reference herein in their entirety.

FIELD OF THE INVENTION

The present invention concerns methods, compounds, compositions, and kits useful for the treatment of cancer, and in particular, breast cancer, in a subject in need thereof.

BACKGROUND OF THE INVENTION

Breast cancer accounts for approximately 25% of all new cancer cases diagnosed among women annually, and it is the second leading cause of cancer-related death among women. Ninety percent of all cancer-related deaths occur not as a result of the primary tumor, but of complications associated with metastasis. There are no agents available for the specific treatment of the metastatic process.

SUMMARY OF THE INVENTION

The present invention provides compounds, compositions and methods useful for the treatment of cancer. In particular, the present invention provides methods of treating cancer, comprising administering to a subject an effective amount of a mitochondrially-targeted electrophilic (MTE) compound. In particular embodiments, the MTE compound is iodobutyl triphenylphosphonium iodide (IBTP) or an analog thereof.

Embodiments of the present invention further provide methods of preventing or reducing metastasis, comprising administering to a subject an effective amount of a mitochondrially-targeted electrophilic (MTE) compound as described herein.

Embodiments of the present invention also provide compounds having the following structure:

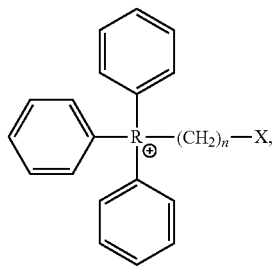

wherein R is an ammonium, sulfonium or phosphonium cation; n is 1, 2, 3, 4, 5, 6, 7, 8, 9, 10, 11, 12, 13, 14 or 15; and X is I, Br, Cl or mesylate.

Further embodiments of the present invention provide pharmaceutical compositions comprising the compounds described herein and a pharmaceutically acceptable carrier, excipient or diluent, or combination thereof.

Embodiments of the present invention also provide kits comprising the compositions described herein and a container suitable for housing or delivery of the composition within a common packaging, and instructions for use of the same.

DETAILED DESCRIPTION

Figure 1:
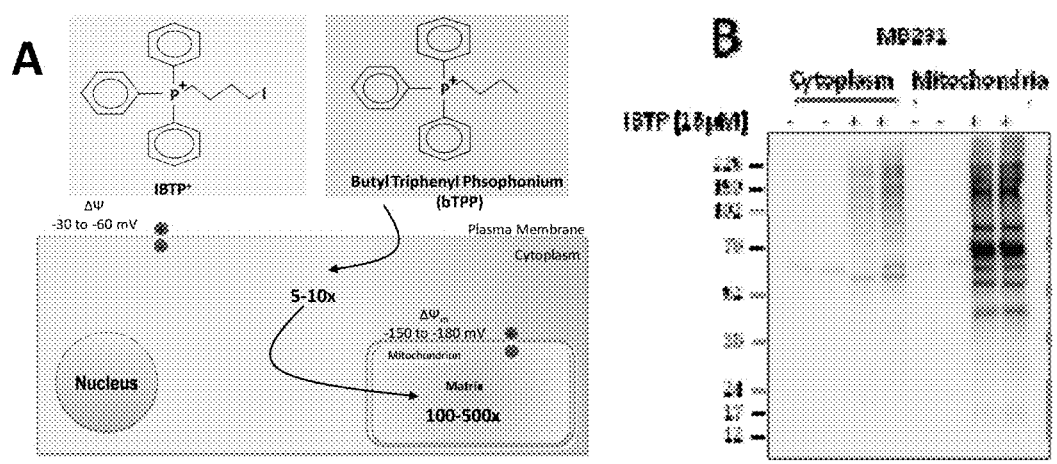
FIG. 1. Accumulation and adduct formation of MTEs. Panel A TPP compounds accumulate within the mitochondrion 100-500× based on the membrane potential. Within the mitochondrion, electrophilic analogs are able to form covalent adducts with proteins containing deprotonated cysteine residues (e.g. those with low pKa of the thiol group). Panel B MDA MB-231 cells were treated by addition of 15 µM IBTP (+) or bTPP (−) to media for 4 h at 37° C. Cells were fractionated into mitochondria and cytoplasmic fractions by differential centrifugation. Protein adducts were detected by Western blot analysis using an antibody raised against the triphenylphosphonium moiety.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention pertains. The terminology used in the description of the invention herein is for the purpose of describing particular embodiments only and is not intended to be limiting of the invention. As used in the description of the invention and the claims set forth herein, the singular forms "a," "an," and "the" are intended to include the plural forms as well, unless the context clearly indicates otherwise.

All publications and other references cited herein are incorporated by reference in their entireties for the teachings relevant to the sentence and/or paragraph in which the reference is presented.

"Effective amount" as used herein refers to an amount of a compound, composition or formulation of the invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation.

By the term "treat," "treating" or "treatment of" (and grammatical variations thereof) it is meant that the severity of the subject's condition is reduced, at least partially improved or ameliorated and/or that some alleviation, mitigation or decrease in at least one clinical symptom is achieved and/or there is a delay in the progression of the disease or disorder.

A "treatment effective" amount as used herein is an amount that is sufficient to treat (as defined herein) the subject. Those skilled in the art will appreciate that the therapeutic effects need not be complete or curative, as long as some benefit is provided to the subject.

The term "prevent," "preventing" or "prevention of" (and grammatical variations thereof) refer to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. In representative embodiments, the term "prevent," "preventing," or "prevention of" (and grammatical variations thereof) refer to prevention and/or delay of the onset and/or progression of a metabolic disease in the subject, with or without other signs of clinical disease. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present invention.

Examples of cancers, tumors, and neoplastic tissue (all of which can be prevented or treated using the methods of the present invention) include, but are not limited to, malignant disorders such as breast cancers, osteosarcomas; angiosarcomas; fibrosarcomas and other sarcomas; leukemias; lymphomas; sinus tumors; ovarian, uretal, bladder, prostate and other genitourinary cancers; colon, esophageal and stomach cancers and other gastrointestinal cancers; lung cancers; myelomas; pancreatic cancers; liver cancers; kidney cancers; endocrine cancers; skin cancers; and brain or central and peripheral nervous (CNS) system tumors, malignant or benign, including gliomas and neuroblastomas.

As used herein, a "pharmaceutically acceptable carrier" according to the present invention is a component such as a carrier, diluent, or excipient of a composition that is compatible with the other ingredients of the composition in that it can be combined with the compounds and/or compositions of the present invention without eliminating the biological activity of the compounds or the compositions, and is suitable for use in subjects as provided herein without undue adverse side effects (such as toxicity, irritation, allergic response, and death). Side effects are "undue" when their risk outweighs the benefit provided by the pharmaceutical composition. Non-limiting examples of pharmaceutically acceptable components include, without limitation, any of the standard pharmaceutical carriers such as phosphate buffered saline solutions, water, emulsions such as oil/water emulsions or water/oil emulsions, microemulsions, and various types of wetting agents.

"Kit" as used herein refers to an assembly of components. The assembly of components can be a partial or complete assembly.

As used herein, "administered with" means that the compounds of the present invention and at least one other adjuvant or chemotherapeutic agent as known to those skilled in the art (such as alkylating agents, antimetabolites, anthracyclines, plant alkaloids, topoisomerase inhibitors, cytotoxic antibiotics and other antitumor agents) are administered at times sufficiently close that the results observed are indistinguishable from those achieved when the compounds are administered at the same point in time. The compounds can be administered simultaneously (i.e., concurrently) or sequentially. Simultaneous administration can be carried out by mixing the compounds prior to administration, or by administering the compounds at the same point in time. Such administration can be at different anatomic sites or using different routes of administration. The phrases "concurrent administration," "administration in combination," "simultaneous administration" or "administered simultaneously" can also be used interchangeably and mean that the compounds are administered at the same point in time or immediately following one another. In the latter case, the two compounds are administered at times sufficiently close that the results produced are synergistic and/or are indistinguishable from those achieved when the compounds are administered at the same point in time. Alternatively, the compounds of this invention can be administered separately from the administration of an adjuvant or chemotherapeutic agent prior to an initial round of chemotherapy, during chemotherapy or after chemotherapy.

The active compounds described above can be formulated for administration in accordance with known pharmacy techniques. See, e.g., Remington, *The Science And Practice of Pharmacy* ($9^{th}$ Ed. 1995). In the manufacture of a pharmaceutical composition according to the present invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier can be a solid or a liquid, or both, and is preferably formulated with the compound as a unit-dose formulation, for example, a tablet, which can contain from 0.01% or 0.5% to 95% or 99%, or any value between 0.01% and 99%, by weight of the active compound. One or more active compounds can be incorporated in the compositions of the invention, which can be prepared by any of the well-known techniques of pharmacy, comprising admixing the components, optionally including one or more accessory ingredients. Moreover, the carrier can be preservative free, as described herein above.

In some embodiments, the compounds provided by the present invention comprises a lower limit ranging from about 0.01, 0.02, 0.03, 0.04, 0.05, 0.06, 0.07, 0.08, 0.09, 1.0, 2.0, 3.0, 4.0, 5.0, 6.0, 7.0, 8.0, 9.0, and 10% to an upper limit ranging from about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100% by weight of the composition.

The formulations of the present invention can include those suitable for oral, rectal, topical, buccal (e.g., sublingual), vaginal, parenteral (e.g., subcutaneous, intramuscular, intradermal, intravenous, or intrathecal), topical (i.e., both skin and mucosal surfaces, including airway surfaces) and transdermal administration, although the most suitable route in any given case will depend on the nature and severity of the condition being treated and on the nature of the particular active compound which is being used.

Routes of parenteral administration may include intrathecal injection and intraventricular injection into a ventricle of the brain in a resection cavity.

Formulations suitable for oral administration can be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations can be prepared by any suitable method of pharmacy which includes bringing into association the active compound and a suitable carrier (which can contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet can be prepared by compressing or molding a powder or granules containing the active compound, optionally with one or more accessory ingredients. Compressed tablets can be prepared by compressing, in a suitable machine, the compound in a free-flowing form, such as a powder or granules optionally mixed with a binder, lubricant, inert diluent, and/or surface active/ dispersing agent(s). Molded tablets can be made by molding, in a suitable machine, the powdered compound moistened with an inert liquid binder.

Formulations of the present invention suitable for parenteral administration comprise sterile aqueous and non-aqueous injection solutions of the active compound, which preparations are preferably isotonic with the blood of the intended recipient. These preparations can contain, buffers and solutes which render the formulation isotonic with the blood of the intended recipient. Aqueous and non-aqueous sterile suspensions can include suspending agents and thickening agents. The formulations can be presented in unit\dose or multi-dose containers, for example sealed ampoules and vials, and can be stored in a freeze-dried (lyophilized) condition requiring only the addition of the sterile liquid carrier, for example, saline or water-for-injection immediately prior to use. Extemporaneous injection solutions and suspensions can be prepared from sterile powders, granules and tablets of the kind previously described.

For example, in one aspect of the present invention, there is provided an injectable, stable, sterile composition comprising active compounds, or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable can be employed in sufficient quantity to emulsify the compound or salt in an aqueous carrier. Non-limiting examples of agents that contribute to the pharmaceutical acceptability of the compositions of the present invention include normal saline, phosphatidyl choline, and glucose. In some embodiments, the pharmaceutically acceptable carrier can be normal saline. In other embodiments, the pharmaceutically acceptable carrier can be normal saline with up to 0.0, 0.01, 0.02, 0.03, 0.04, 0.05, 0.06, 0.07, 0.08, 0.09, 1.0, 2.0, 3.0, 4.0, 5.0, 6.0, 7.0, 8.0, 9.0, 10, 11, 12, 13, 14, 15, 16, 17, 18, 19, and 20%, and any value between 0.01% and 20%, glucose.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, *Pharmaceutical Research* 3(6):318 (1986)) and typically take the form of an optionally buffered aqueous solution of the active compound. Suitable formulations comprise citrate or bis\tris buffer (pH 6) or ethanol/ water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same can be incorporated into lipid vesicles. In such an instance, due to the water solubility of the compound or salt, the compound or salt will be substantially entrained within the hydrophilic center or core of the liposomes. The lipid layer employed can be of any conventional composition and can either contain cholesterol or can be cholesterol-free. When the compound or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques.

The liposomal formulations containing the compounds disclosed herein or salts thereof, can be lyophilized to produce a lyophilizate which can be reconstituted with a pharmaceutically acceptable carrier, such as water, to regenerate a liposomal suspension.

Other pharmaceutical compositions can be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active agents or their salts, the pharmaceutical compositions can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions can contain microbial preservatives. Useful microbial preservatives include methylparaben, propylparaben, and benzyl alcohol. The microbial preservative is typically employed when the formulation is placed in a vial designed for multidose use. The pharmaceutical compositions of the present invention can be lyophilized using techniques well known in the art.

Subjects suitable to be treated according to the present invention include, but are not limited to, avian and mammalian subjects, and are preferably mammalian. Mammals of the present invention include, but are not limited to, canines, felines, bovines, caprines, equines, ovines, porcines, rodents (e.g. rats and mice), lagomorphs, primates, humans, and the like, and mammals in utero. Any mammalian subject in need of being treated according to the present invention is suitable. Human subjects are preferred. The human subjects may be male or female and may be of any race or ethnicity, including, but not limited to, Caucasian, African-American, African, Asian, Hispanic, Indian, etc. The subjects may be of any age, including newborn, neonate, infant, child, adolescent, adult, and geriatric.

A subject of this invention is any subject in whom prevention and/or treatment of a metabolic disorder is needed or desired, as well as any subject prone to a metabolic disorder. In some embodiments, the subject is a human; however, a subject of this invention can include an animal subject, particularly mammalian subjects such as canines, felines, bovines, caprines, equines, ovines, porcines, rodents (e.g: rats and mice), lagomorphs, primates (including non-human primates), etc., for veterinary medicine or pharmaceutical drug development purposes.

Illustrative avians according to the present invention include chickens, ducks, turkeys, geese, quail, pheasant, ratites (e.g., ostrich) and domesticated birds (e.g., parrots and canaries), and birds in ovo.

The present invention is primarily concerned with the treatment of human subjects, but the invention can also be carried out on animal subjects, particularly mammalian subjects such as mice, rats, dogs, cats, livestock and horses for veterinary purposes, and for drug screening and drug development purposes. Suitable subjects include subjects in need thereof, at risk for cancer, diagnosed with cancer and/or undergoing chemotherapy.

A. Breast Cancer Cells and Susceptibility to MTEs
Significance

Breast cancer is a major cause of mortality for women in the United States. Key problems in treating breast cancer relate to the fact that certain subtypes of breast cancer (e.g. basal-like, triple-negative) and breast cancer stem cells exhibit resistance to front-line chemotherapeutics.

These compounds will be tested using a translational approach involving cell and animal models in order to accomplish two goals 1) to prevent metabolic adaptation of breast cancer cells to hypoxia, and 2) to sensitize cancer cells to apoptosis. The experiments will use a panel of breast cancer cell lines and stem cells representing different subtypes in in vitro cell culture models, and in orthotopic xenograft models of breast cancer tumorigenesis.

Innovation

This unique conceptual approach will address the problem of chemoresistance in cancer cells by targeting bioenergetic adaptation to hypoxia, and sensitizing tumorigenic cells to apoptosis. An increased understanding of specific and regulated cell signaling which occurs by redox modulation of mitochondrial proteins will likely lead to truly novel therapeutic approaches for cancer treatment.

Approach

Previous studies from our laboratory have shown that redox active electrophilic compounds form covalent adducts with specific proteins, and modulate cellular function by altering specific signaling pathways. In a recent study, we have shown that an electrophilic lipid, 15 deoxy-prostaglandin $J_2$ (15d-$PGJ_2$) inhibits migration of breast cancer cells by altering p38 and ERK signaling (1). We also developed a mitochondrially-targeted analog of 15d-$PGJ_2$ (mito-15d-$PGJ_2$) and showed that mitochondrial targeting increased the apoptotic efficacy and prevented upregulation of endogenous antioxidant defenses (2). More recently we have focused on mitochondrially-targeted electrophiles (MTEs) which are based on the premise that lipophilic, cationic molecules accumulate within the mitochondrion according to the mitochondrial membrane potential (3, 4). Molecular strategies to target the mitochondrion utilize the unique biochemical properties of the organelle. Actively respiring mitochondria have an electrochemical gradient due to proton pumping from the matrix to the intermembrane space. This results in a membrane potential ($\Delta\Psi$) which is used by ATP synthase (Complex V) to convert ADP to ATP. Agents which contain a delocalized positively charged moiety, such as triphenyl phosphonium, can be accumulated within the mitochondrion based on $\Delta\Psi$. Depending on the mitochondrial membrane potential, these compounds can reach concentrations between 100 and 500 fold higher than outside the cell (5). Therefore, cells with highly active mitochondria will have a higher membrane potential, and will accumulate more MTE molecules than cells with less active mitochondria. Indeed, Li et al. recently showed that triphenyl phosphonium-containing radiolabeled agents selectively accumulate within the mitochondrion in a rat model of breast carcinoma (6).

The goal of this study is to systematically determine which breast cancer subtypes are susceptible to MTEs, and to determine the mechanisms by which MTEs inhibit bioenergetic adaptation to hypoxia and elicit chemosensitization. While the information obtained from this study will be a combination of descriptive and mechanistic, it will be the first comprehensive analysis of this class of agents (i.e. MTEs) in breast cancer. These results will likely lead to discovery of novel drugs and/or drug leads, but perhaps more importantly, may serve as a new pathway for future research in breast cancer by providing a new targeting strategy involving critical functional pathways used by cancer cells.

Hypothesis 1.

Specific breast cancer cell and stem cell subtypes exhibit altered mitochondrial bioenergetics during hypoxia making them more susceptible to MTEs (mitochondrially-targeted electrophiles).

Aim 1. To Determine which Breast Cancer and Stem Cell Subtypes (Basal, Luminal, HER2-Amplified Luminal (ER+/−), HER2-Amplified Basal (ER−) are Susceptible to MTEs In Aim 1, the bioenergetic responses of 26 breast cancer cell lines and representative breast cancer stem cells to dynamic changes in oxygen tension will be determined. A panel of MTEs will be synthesized with variations in hydrophobicity and reactivity. These agents will be tested to determine their effects on cell viability, sensitization to doxorubicin or Abraxane, and the ability to inhibit malignant features such as cell adhesion, invasion, and angiogenesis under normoxia and hypoxia. These experiments will determine which cancer subtypes may serve as the best candidates for MTEs. Metabolic function will be determined using extracellular flux analyses under ambient air ("normoxia") and at various oxygen tensions as low as 1% $O_2$ ("hypoxia"). Bioenergetics will be determined in real time using live, adherent cancer cells using an extracellular flux analyzer (Seahorse Biosciences) which is installed within a controlled oxygen chamber. Using this method, oxygen consumption attributable to ATP synthesis, proton leak, and reserve respiratory capacity can be determined. In addition, extracellular acidification due to lactate can be used to determine glycolytic flux. We have experience with the proposed bioenergetic measurements using extracellular flux analysis in normoxia, hypoxia, and under dynamic oxygen conditions with triple-negative breast cancer cells, and in a variety of cell types (7-10).

Justification and Feasibility (Aim 1)

Figure 2:
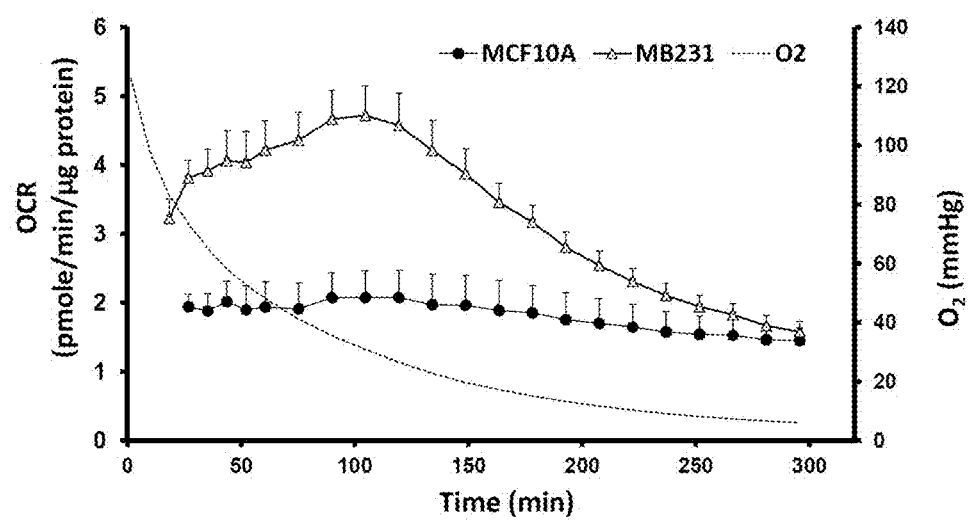
FIG. 2. Bioenergetic response of breast cancer cells to decreasing $O_2$ tension. OCR was determined in MDA-MB-231 (open symbols) and nontumorigenic MCF10A cells (closed symbols) over time at decreasing oxygen tensions ranging from near ambient $O_2$ to 1% $O_2$ (dotted line).

It has been previously demonstrated that triple-negative breast cancer cells exhibit a unique bioenergetic profile as oxygen is gradually removed from the environment (11) (in press, see Appendix 1) FIG. 2 shows the bioenergetic profile which is characterized by a paradoxical increase in oxygen consumption rate (OCR) at 4-5% oxygen, followed by a decrease in OCR at oxygen tensions below 4% where, as expected, oxygen becomes limiting at complex IV of the respiratory chain. The increase in OCR is accompanied by increased glycolysis as evidenced by an extracellular acidification rate (ECAR) due to lactate production into the extracellular medium. These results were recently accepted for publication in *PLoS One* (in press) (11).

Mitochondrially-Targeted Electrophiles.

Figure 3:
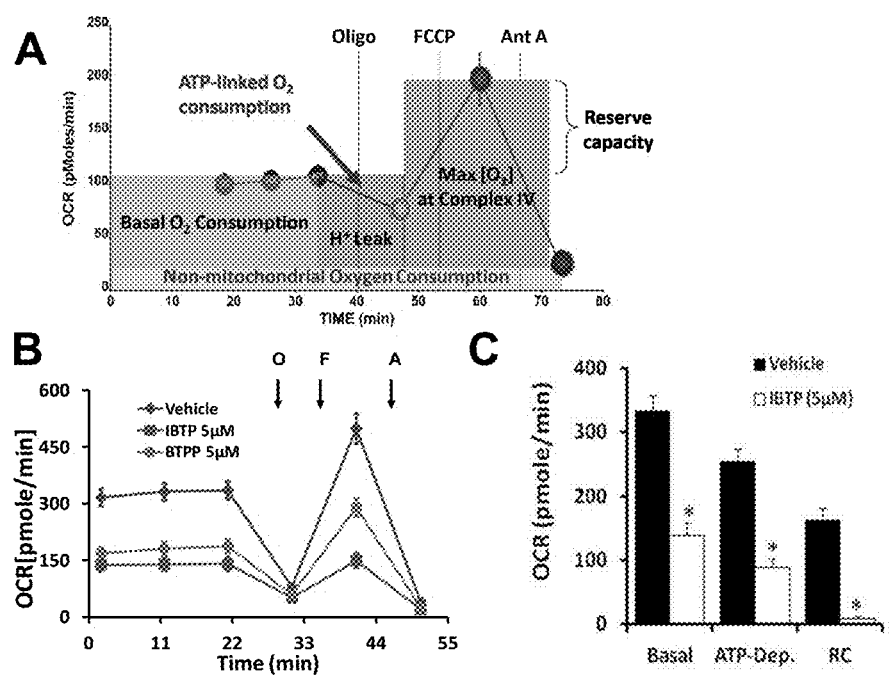
FIG. 3. Bioenergetic response of breast cancer cells to MTE. Panel A. A schematic representation of the mitochondrial bioenergetic assay in an Extracellular Flux Analyzer XF-24 (Seahorse Biosciences). Panel A: Sequential injections of oligomycin, FCCP, and Antimycin A allow determination of the component mitochondrial bioenergetic parameters. Panel B. MDA-MB 231 cells were treated for 4 h in 0.5% serum containing medium with EtOH vehicle, IBTP (5 µM), or BTPP (5 µM) and the OCR measured over time. Panel C. Comparison of basal OCR, ATP-dependent OCR, and reserve capacity (RC) with veh and IBTP treatments. Each point is the mean of a minimum of 3 determinations±SEM, from at least 2 independent experiments. Asterisks represent p<0.05.

Recent work has shown that MTEs can modulate cell signaling, and depending upon the specific MTE, may do so without causing overt cellular toxicity to cancer cells or normal cells (12). MTEs are small molecules which consist of a triphenylphosphonium lipophilic cationic moiety and a leaving group such as iodide, which renders the adjacent carbon electrophilic. These compounds form covalent adducts to a select group of proteins, and target proteins which have been identified include enzymes within the Krebs cycle (aconitase, isocitrate dehydrogenase, and α-ketoglutarate dehydrogenase)(13). Preliminary studies in the PI's laboratory demonstrate that a model MTE, iodobutyl triphenylphosphonium (IBTP) decreases OCR, particularly reserve capacity. We have previously shown reserve capacity is indicative of the cells' ability to withstand a "second hit" of oxidative stress (7). FIG. 3 shows the effects of IBTP compared with the non-electrophilic analog butyl triphenyl-phosphonium (bTPP). FIG. 3, Panel A shows the bioenergetic assay and the addition of compounds oligomycin, FCCP, and antimycin A which are used to determine the OCR attributable to parameters of mitochondrial bioenergetic function. FIG. 3, Panel B shows that both IBTP and bTPP decrease basal OCR, but that IBTP completely abrogates the reserve capacity (FIG. 3, Panel C, "RC").

Figure 4:
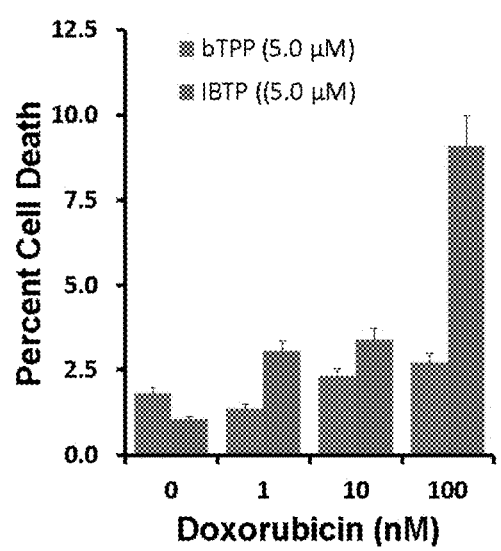
FIG. 4. Effect of MTE on doxorubicin-induced cell death. MDA-MB 231 cells were treated with 10 µM IBTP or bTPP for 4 h and treated with different doses of DOX for 18 h. Cytotoxicity determined by LDH activity release. No significant cell death was observed in cells treated with EtOH vehicle at these concentrations of doxorubicin.

Additional preliminary studies suggest that MTEs are effective at chemosensitizing breast cancer cells. FIG. 4 shows the effects of IBTP on cell death (measured by LDH release) in response to doxorubicin. Interestingly, IBTP did not sensitize MCF10A nontumorigenic cells to doxorubicin, and IBTP was not cytotoxic to cancer or noncancer cells (data not shown). The fact that IBTP (but not bTPP) decreases reserve capacity suggests that MTEs may weaken cancer cells by inhibiting reserve bioenergetic capacity "RC" (FIG. 3, Panel C), and that this may be important in sensitizing these cells to chemotherapeutics such as doxorubicin and/or Abraxane.

Research Design (Aim 1)

Breast Cancer Cell Lines and Stem Cells:

The cells used for this study will include 26 cells lines representing 6 distinct subtypes of breast cancer (luminal, HER2 amplified luminal (ER+), HER2 amplified luminal (ER−), HER2 amplified basal (ER−), Basal A, Basal B). These cell lines are listed in Table 1. In addition, normal mouse mammary epithelial cells and cardiac myocytes will be tested to determine toxicity in these cell types. Stem cells will be obtained by harvesting one cell line from each subtype to 75% confluence with trypsin and labeling with reagents obtained from StemCell Technologies (Durham, N.C.). Briefly, 1 μl ALDEFLUOR reagent in 100 μl ALDEFLUOR buffer will be added to $5 \times 10^6$ cells and incubated for 30 min. at 37° C. In addition, fluorescent antibodies which recognize CD44 and CD24 will be added. Samples will be analyzed by flow cytometry and cells which are CD44+/CD24−/ALDH+ will be sorted and allowed to recover for 13 h in MEGM medium in ultra-low attachment plates as described (14). These sorted cells will be used for further studies as stem cells.

TABLE 1

Breast cancer lines proposed in this study.

| Phenotype | Cell line | Tumor origin |
|---|---|---|
| Luminal | MCF-7 | Met AC, PE |
| | T-47D | IDC, PE |
| | ZR-75-1 | IDC, AF |
| | MDA-MB-134 | IDC, PE |
| HER2-amplified luminal (ER+) | BT-474 | IDC, 1° |
| | DY36T2 (subclone MDA-MB-361) | Met AC, BR |
| | ZR-75-30 | IDC, AF |
| HER2-amplified luminal (ER−) | MDA-MB-453 | MC, PE |
| | SK-BR-3 | AC, PE |
| HER2-amplified basal (ER−) | HCC1569 | Met C, 1° |
| | HCC1954 | DC, 1° |
| TNBC (basal A) | MDA-MB-468 | Met AC, PE |
| | HCC1187 | DC, 1° |
| | BT-20 | AC, 1° |
| | HCC1937 | DC, 1° |
| | HCC1143 | DC, 1° |
| | HCC1599 | DC, 1° |
| TNBC (basal B) | SUM149 | Inf DC, 1° |
| | HCC38 | DC, 1° |
| | 2LMP (subclone MDA-MB-231) | LM |
| | SUM159 | AnCa, 1° |
| | MDA-MB-436 | AC, PE |

TABLE 1-continued

Breast cancer lines proposed in this study.

| Phenotype | Cell line | Tumor origin |
|---|---|---|
| | SUM102 | Int DC, 1° |
| | MDA-MB-157 | Med, PE |
| | BT-549 | IDCp, 1° |
| | MDA-MB-231 | Met AC, PE |

Tumor type:
AC adenocarcinoma;
AnCa anaplastic carcinoma;
DC ductal carcinoma;
IDC invasive ductal carcinoma;
IDCp invasive ductal carcinoma, papillary;
Inf DC inflammatory ductal carcinoma,
Int DC intraductal carcinoma,
Med medullary carcinoma;
Met AC metastatic adenocarcinoma,
Met C metaplastic carcinoma,
MC metastatic carcinoma
Source:
1° primary tumor,
AF ascetic fluid,
BR brain metastasis;
LM lung metastasis;
PE pleural effusion,
PF pericardial effusion Subaim 1.1 Design and Synthesis of MTEs:

A panel of MTEs will be designed based on IBTP used in the preliminary studies, in an effort to identify an MTE which has greater efficacy against breast cancer cells and stem cells. These compounds will be synthesized. IBTP used in the preliminary studies was produced in his laboratory following a published procedure (15). IBTP contains a 4-carbon alkyl chain and an iodo leaving group. In designing the panel of MTEs we will determine whether MTEs with longer or shorter alkyl chain spacer groups are more effective at inhibiting the biological endpoints in this proposal. MTEs with 3-, 6-, 8-, and 10-carbon alkyl chains and iodo leaving groups will be synthesized. Additional IBTP required for these studies will also be synthesized. The target compounds will be synthesized following a similar procedure by treating triphenyl phosphine with 1,3-diiodoethane, 1,4-diiodobutane, 1,6-diiodohexane, 1,8-diiodooctane or 1,10-diiododecane to form the 3-, 4-, 6-, 8-, and 10-carbon alkyl groups, respectively.

The leaving groups of selected electrophiles will be modulated in order to optimize the reactivity of the compound. Iodo-leaving groups will be used in initial experiments, and worse leaving groups such as Cl or Br and better leaving groups such as organic mesylates will be synthesized and tested based on the chosen alkyl chain backbone determined in initial experiments. Triphenyl phosphine will be treated with chloro- or bromo-derivatives of iodobutane to form electrophiles with chloro- or bromo-leaving groups. Triphenyl phosphine will be treated with iodobutanol to form an intermediate compound, which in turn will be treated with methane sulfonyl chloride in the presence of $Et_3N$ to form a mesylate leaving group. Purity of all of target compounds will be evaluated by $^1$H-NMR, $^{13}$C-NMR and MS to be sure that they meet purity criteria (99.9%) before subjected to biological evaluation. A total of 5 iodo-based alkyl chain analogs, and 3 leaving group analogs are expected to be synthesized.

Subaim 1.2 Bioenergetic Adaptation to Hypoxia:

Hypoxic adaptation will be measured using a Seahorse Extracellular Flux Analyzer (XF96). This technique simultaneously measures oxygen consumption rate (OCR) and extracellular acidification rate (ECAR) in the medium immediately surrounding cultured adherent cells as described previously (2). Adherent breast cancer cells or stem cells derived from these cell lines will be obtained from a source, who has previously characterized these cells in an independent study (16). Cells will be subcultured onto XF analyzer culture plates at an optimal cell density, which will be determined empirically. Our previous experience suggests that $4 \times 10^5$ cells will be needed per well. Concentrations of oligomycin (an ATP synthase inhibitor), FCCP (a mitochondrial uncoupler) and Antimycin A (Complex III inhibitor) will each be confirmed in each cell type, and optimized if necessary. Basal oxygen consumption rate (OCR), ATP-linked OCR, protein leak, maximal respiratory capacity, and reserve respiratory capacity will be determined as previously described (7). The rate of extracellular acidification (ECAR) will be measured simultaneously with OCR prior to addition of mitochondrial inhibitors. 2-deoxy-D-glucose will be used to demonstrate the specific contribution of glycolysis to ECAR. Protein concentration from each well will be determined by the method of Bradford (Bio-Rad) and rates will be normalized to protein within each well.

Subaim 1.3 Chemosensitization:

To study the effect of MTEs on the survival of highly metastatic breast cancer cells under hypoxia, we will use a panel of breast cancer cell lines and stem cells as described previously (see Table 1 and (16) to establish that MTEs can be used to chemosensitize breast cancer cells and stem cells. These cells are available from a source. The effect of MTEs on the survival of breast cancer cells under normoxia and hypoxia will be determined. The data obtained for the cells treated with MTEs under hypoxia (1%) will be compared with that of cells treated with MTEs under normoxia (21% $O_2$). The effect of MTEs will also be compared in combination with chemotherapeutic drugs doxorubicin or Abraxane under normoxia as well as hypoxia. Cells will be pretreated for 4 h with MTEs, which we have previously shown is sufficient for protein adduct formation. The highest non-toxic dose of MTE will be selected and dose curves will be generated for doxorubicin or Abraxane (0-100 µM) over a time course ranging from 12-36 h. Viability will be determined using LDH release assay, and key results confirmed using trypan blue exclusion, caspase cleavage, and clonogenic survival assays. The $IC_{50}$ for each chemotherapeutic will be determined with each cell line. All experiments will be performed in triplicate and replicated a minimum of 3 independent times. Statistical analyses will include ANOVA and appropriate post-test analyses in consultation with the Biostatistics Core of the Comprehensive Cancer Center here at UAB. $IC_{50}$ for doxorubicin will be determined for all viability curves and conditions which cause a significant decrease in $IC_{50}$ will be defined as sensitizing cells to doxorubicin toxicity.

Subaim 1.4 Malignant Features (Adhesion, Invasion, Angiogenesis):

Adhesion:

Cell adhesion will be determined in breast cancer cell lines and stem cells (see Table 1). $2 \times 10^5$ cells/plate will be seeded on 6-well plates, and after 24 h cells will be starved in 0.5% fetal calf serum-containing media for another 24 h. Cells will then be treated with a dose range of MTE analogs (described in subaim 1.1) ranging from 0-25 µM for another 24 h. Non-electrophilic analogs will be used as controls, and are available commercially. Viability will be determined for each concentration using LDH release assay, and key results confirmed using trypan blue exclusion and caspase cleavage.

Non-lethal doses will be used for time course experiments and cells will be treated with a fixed concentration of the analogs for times ranging from 1 h-18 h. Cells will be scraped and made into single cell suspension, then counted and plated in a 100 mm tissue culture plate. After 24 h the media will be collected, centrifuged and the viable cells counted using trypan blue.

Invasion:

The invasive potential of breast cancer cells under hypoxia will be assessed in vitro in matrigel-coated invasion Chambers (BD BioCoat Matrigel Invasion Chamber) in accordance with the manufacturer's instructions. In this assay, tumor cells must overcome a reconstituted basement membrane by a sequential process of proteolytic degradation of the substrate and active migration. Trypsinized and pelleted cells will be resuspended to a final concentration of $5\times10^5$ cells in 500 µl serum-free media in each insert and treated with MTE or ethanol vehicle. Medium containing 10% FCS will be used as a chemo-attractant in the companion plate. After incubation at normoxia or hypoxia, the non-invasive cells will be removed from the upper surface of the membrane, and the invasive cells on the under surface of the membrane will be stained and counted microscopically at 100× magnification. Five fields per membrane will be randomly selected and counted in each group (17). The percentage of invasive cells will be calculated for each group as the percentage invasion through the matrigel membrane relative to the migration through the control membrane, as described in the manufacturer's instructions.

Angiogenesis:

Tumor cells will be treated with a range of doses of MTE for 24 h under hypoxia or normoxia. The media will be removed and fresh serum free media will be added and incubated further for another 24 h. Conditioned media will collect and concentrated 20× using Amicon Ultra 15 Centrifugal filters. This concentrated media will be diluted back to 1× in endothelial cell media without growth factors and will be used as the media for human umbilical cord endothelial cell proliferation, migration and invasion as described above and tube formation assay for angiogenesis (18). The ability of conditioned media to inhibit angiogenesis will be compared with untreated controls under hypoxia and normoxia.

Expected Outcomes (Aim 1)

For purposes of choosing a lead MTE compound for further study, compounds which exhibit inhibitory activity in all endpoints will be chosen for follow-up. It is possible that altering the leaving group will change the uptake of the compounds into the mitochondrion and that one or more analogs may not form protein adducts. In the event, that an analog does not alter any of the cellular endpoints, we will test to determine whether the compounds entered the mitochondrion and formed protein adducts by Western blot analysis of the triphenyl phosphonium group in mitochondrially-enriched cellular fractions. If no adducts are found, then an alternate leaving group will be designed, synthesized and tested. However, this is highly unlikely since numerous groups have been added to the triphenyl phosphonium moiety and all compounds reported have been shown to enter the mitochondrion thus far (19). A total of 5 iodo-alkyl chain analogs, and 3 leaving group analogs are expected to be synthesized. However, it may be necessary to design additional analogs based on solubility, excessive toxicity or lack of efficacy.

It is not known precisely which breast cancer subtypes will be susceptible to MTEs, however, it is expected that cells exhibiting higher mitochondrial bioenergetics will accumulate MTEs to a higher extent, and therefore, will be more likely to be inhibited by MTEs. In the event that all cancer cells tested are susceptible, we will chose representative cells lines from each subtype to study in Aims 2 and 3. We anticipate most of the breast cancer cell lines and stem cells will exhibit bioenergetic adaptation (OCR increase) in response to moderate hypoxia (~4% $O_2$), as demonstrated by MDA-MB-231 and MCF10CA metastatic clones. In addition, we expect that MTE treatment will significantly inhibit this bioenergetic adaptation under hypoxia. We also anticipate that MTE treatment will significantly inhibit the ability of hypoxic tumor cells to adhere and invade and also the ability of cancer cells to induce angiogenesis in endothelial cells. We also expect that MTEs will sensitize hypoxic breast cancer cells to doxorubicin and Abraxane in a dose-dependent manner. It is important to note that we do not expect to observe synergy with MTEs and chemotherapeutics in normoxia, since MTEs do not readily cause cell death alone under these conditions. However, at ~4% oxygen, MTEs may cause cell death by inhibiting bioenergetic adaptation to hypoxia, in which case it is likely that MTEs may be synergistic with chemotherapeutics.

Alternative Strategies (Aim 1)

We may use large excess of diiodoalkane reagents (7-10 molar equivalents) in the synthesis. Another potential issue is that MTEs are targeted to the mitochondria, and they may cause changes in the membrane potential which interfere with some assays. For this reason, tetrazolium dyes or dyes that utilize membrane potential to demonstrate the viability cannot be used. In addition, MTEs may decrease cellular adhesion, therefore assays which are dependent on adhesion, such as clonogenic assays, will need to be interpreted in light of this knowledge. If MTEs interfere with these assays, then we will use agar colony formation assay which will secure the cells within agar and allow proliferation.

Hypothesis 2.

MTEs target specific pathways to inhibit hypoxic responses, produce chemosensitization and inhibit malignant features of breast cancer cells.

Aim 2. To Elucidate the Mechanisms by which MTEs Inhibit Hypoxic Responses, Induce Chemosensitization, and Inhibit Malignant Features in Selected Breast Cancer Cell Lines and Stem Cells In Aim 2, the role of HIF-1α and specific known mitochondrial targets of MTEs within the Krebs cycle, e.g., aconitase (ACO), isocitrate dehydrogenase (IDH), and α-ketoglutarate dehydrogenase (KGDH) in mediating anti-cancer effects of MTEs will be determined. Importantly, a human breast cancer tissue microarray will be screened for ACO, IDH and KGDH to determine the abundance of these potential targets of MTEs in human breast cancers.

Justification and Feasibility (Aim 2)

Figure 5:
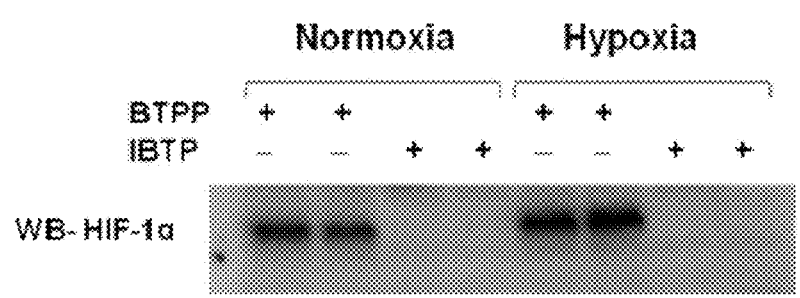
FIG. 5. Effects of an MTE on HIF-1α. MDA-MB-231 cells were incubated for 8 h under normoxia or hypoxia and were treated with either 10 µM IBTP or bTPP for 4 h. The lysates were collected and analyzed for HIF-1α stabilization by western blotting. IBTP also inhibited basal HIF-1α stabilization both time and dose-dependently (data not shown).
Figure 6:
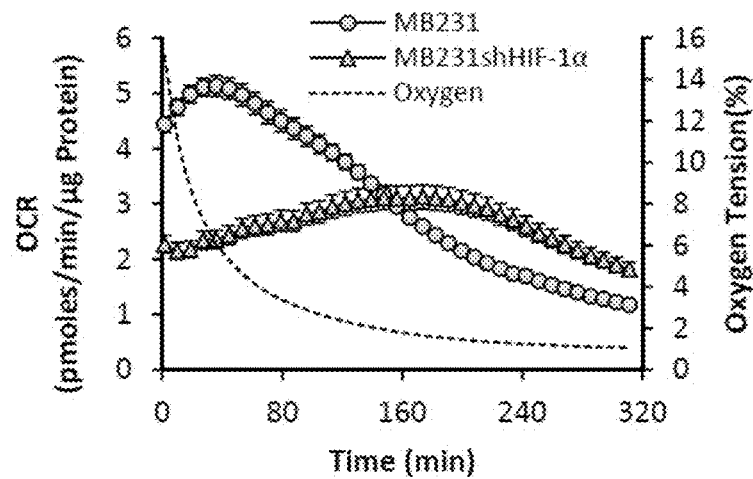
FIG. 6. Effect of HIF-1α on bioenergetic adaptation of MDA-MB-231 cells. MB231 cells (circles) or MB231 cells deficient in HIF-1α (triangles) were exposed to decreasing $O_2$ tension (dotted line).
Figure 7:
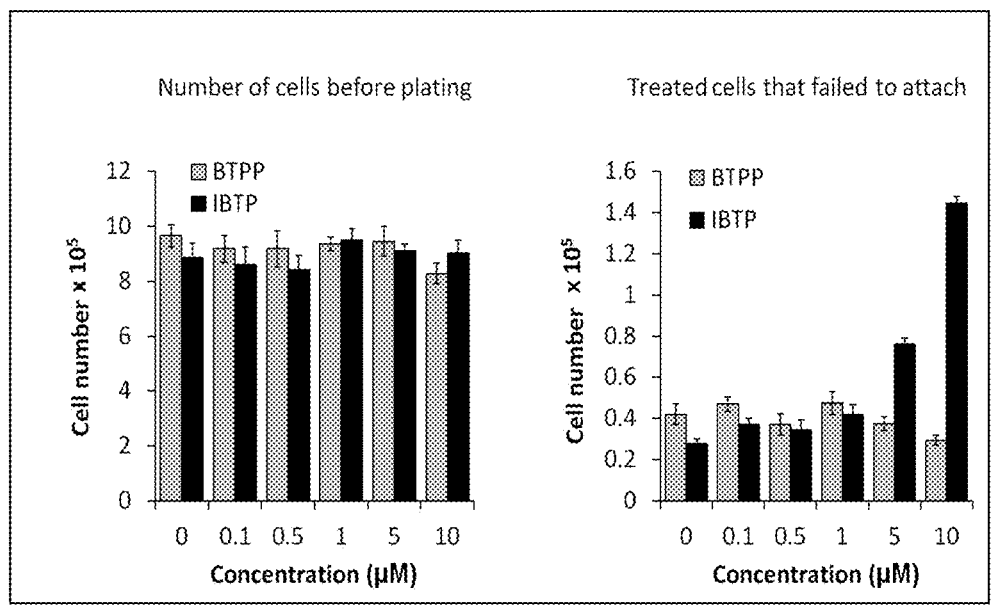
FIG. 7. Two ×$10^5$ cells/plate were plated on a 6-well plate, 24 hrs after plating cells were starved in 0.5% FCS containing media for another 24 hrs. Cells were then treated for another 24 hrs with increasing doses of IBTP or the non-reactive analog butyl-triphenylphosphonium (BTPP) as a control. Cells were scraped and made into single cell suspension. Cells were counted and plated in 100-mm tissue culture plate. After 24 hrs the media is collected, centrifuged and the viable cells were counted using trypan blue.
Figure 8:
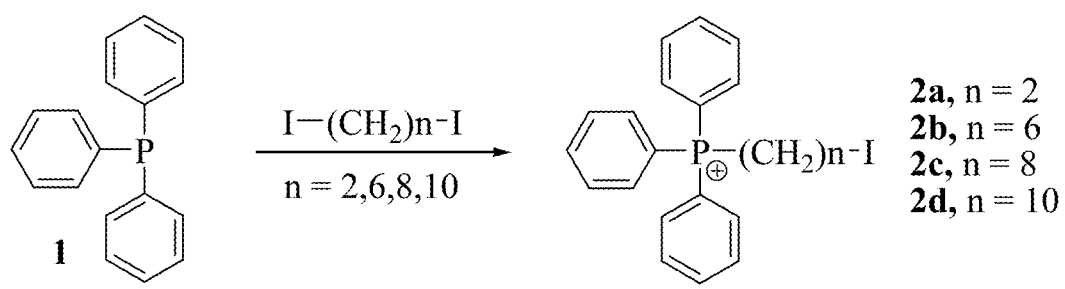
FIG. 8. Synthesis of target compound Class 1.
Figure 9:
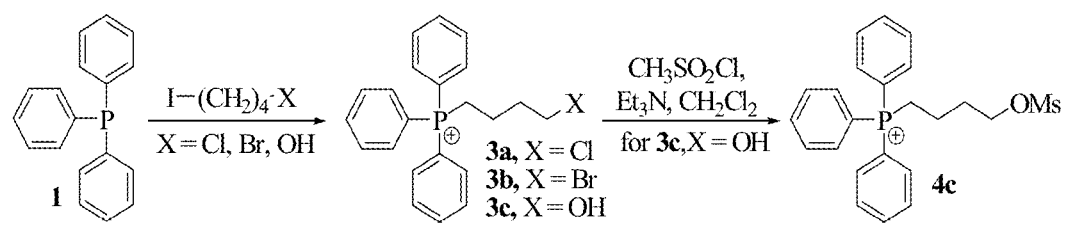
FIG. 9. Synthesis of target compound Class 2.

Our preliminary studies suggest that a model MTE, IBTP, inhibits both constitutive and hypoxia-inducible expression of HIF-1α protein. FIG. 5 shows that expression of HIF-1α protein is decreased after treatment of MDA-MB-231 cells with an MTE (IBTP). However, the mechanism for this decrease in HIF-1α protein is not clear. One possibility is that IBTP inhibits the enzyme within the Krebs cycle, KGDH, that is responsible for converting α-ketoglutarate to succinyl-CoA. Inhibition of this enzyme would cause an increase in α-ketoglutarate, which is a cofactor for the prolyl hydroxylase involved in HIF-1α degradation. We propose that MTEs affect HIF-1α stabilization at least in part, by modulating the activity of KGDH and increasing intracellular levels of α-ketoglutarate. KGDH was previously shown to be among the proteins which form covalent adducts with IBTP (13). Importantly, decreased stabilization of HIF-1α prevents the bioenergetic adaptation to hypoxia in breast cancer cells, as we have recently shown (11)(in press, see Appendix 1). FIG. 6 shows that silencing of HIF-1α expression by stable transfection of shRNA decreases basal OCR (time=0 min), and abolishes the increase in OCR observed as $O_2$.

Though the time scale is slightly different than shown in FIG. 2, the bioenergetic phenomenon is reproducible at ~4% $O_2$, and is completely abrogated by the silencing of HIF-1α, demonstrating that this effect is HIF-1α dependent.

Research Design (Aim 2)

Subaim 2.1. Role of HIF-1α:

The fact that MTEs decrease HIF-1α protein levels, combined with the observation that HIF-1α mediates the bioenergetic adaptation to hypoxia suggests that HIF-1α may be an important mechanism of action for MTEs against breast cancer cell function. Our results showed that HIF-1α protein is required for bioenergetic adaptation, but did not determine whether transcriptional activity is necessary. A first step in determining the role of HIF-1α is to determine whether HIF-1α transcriptional activity is required bioenergetic adaptation to hypoxia. This will be accomplished by silencing HIF-10 and measuring the OCR in response to decreasing oxygen.

In order to determine the role of HIF-1α protein degradation in mediating the effects of MTEs, HIF-1α protein degradation will be prevented by silencing the pVHL ubiqutin ligase, or the prolyl hydroxylase, both of which are involved in HIF-1α degradation. These degradation-resistant HIF-1α clones should be refractory to MTEs. Silencing will be accomplished by transfecting plasmids carrying shRNAs specific for human VHL or prolyl hydroxylase. Plasmids will be purchased from Open Biosystems. To generate stable cell lines, 5 µg of plasmid or empty vector (pLKO.1) will be transfected into selected breast cancer cell subtypes and stem cell subtypes determined in Aim 1 with the FuGENE 6 transfection reagent. Two days after transfection, cells will be selected with 2 µg/ml puromycin for an additional 4 weeks. Clones will be assayed for protein expression by immunoblotting with antibodies against pVHL or prolyl hydroxylase. Several positive clones will be expanded, and clones with the highest HIF-1alpha expression will be chosen for further use in this study. These clones will be characterized in assays for bioenergetic response to hypoxia, chemosensitization, and inhibition of malignant features as described in Aim 1. Susceptibility to selected MTEs will also be determined as described in Aim 1.

Subaim 2.2 Role of Metabolites:

Since MTEs have been shown to form covalent adducts with Krebs cycle proteins (13), it is possible that alterations in metabolite levels are responsible for the anti-cancer effects of MTEs. In this subaim, the metabolome will be monitored in response to MTEs, and the effects of MTEs will be mimicked by exogenous addition of specific metabolites where applicable (e.g. 2-oxoglutarate analog).

Metabolomics:

Breast cancer cells or stem cells will be seeded in 6-well culture plates and grown to a percent confluency similar to that determined in the bioenergetics experiments. Metabolites (glucose 6-phosphate, fructose 6-phosphate, fructose 1,6-bisphosphate, lactate, pyruvate, citrate, aconitate, isocitrate, α-ketoglutarate, succinate, fumarate, and malate) will be extracted with ice-cold methanol from 5 wells, and a lysate prepared from the remaining well in order to determine protein amount for normalization. Metabolomics will be determined by LC-ESI-MRM-MS from extracts.

Subaim 2.3 Role of Krebs Cycle Enzymes:

It has previously been reported that a model MTE (IBTP) forms covalent adducts with proteins involved in the Krebs cycle: aconitase (ACO), isocitrate dehydrogenase (IDH), and α-ketoglutarate dehydrogenase (KGDH) (13). In this subaim, the role of these known targets of MTEs in mediating the hypoxic response, chemosensitization, and inhibition of malignant features will be determined by silencing each of these targets. Silencing will be accomplished by transfecting plasmids carrying shRNAs specific for ACO2, IDH, or dihydrolipoamide succinyltransferase (DLST; the catalytic subunit of the KGDH complex). Plasmids will be purchased from Open Biosystems. To generate stable cell lines, 5 µg of plasmid or empty vector (pLKO.1) will be transfected into selected breast cancer cell subtypes and stem cell subtypes determined in Aim 1 with the FuGENE 6 transfection reagent. Two days after transfection, cells will be selected with 2 µg/ml puromycin for an additional 4 weeks. Clones will be assayed for protein expression by immunoblotting with antibodies against ACO2, IDH, or DLST. Several positive clones will be expanded, and clones with the lowest protein expression will be chosen for further use in this study. These clones will be assessed in assays for bioenergetic response to hypoxia, chemosensitization, and inhibition of malignant features as described in Aim 1.

Subaim 2.4 Expression of Known Targets of MTEs and HIF-1α in Human Breast Cancer Tissue and Adjacent Normal Tissue:

The expression of ACO, IDH, KGDH, and HIF-1α will be determined in a variety of breast cancer types and normal tissues by immunohistochemistry using a breast cancer tissue microarray. These experiments will assess the possibility that these potential targets are differentially expressed in human breast cancer. A microarray of 218 breast cancers was prepared from tissue obtained from adult women ages 25-89 of any race who had undergone surgery at UAB for breast cancer from 1988 to 1996.

Results will be correlated with a de-identified database containing clinicopathologic data, including patient age, date of diagnosis, tumor size, histologic grade, lymph node status, hormone receptor status, all of which were collected from surgical pathology reports and from review of charts in the UAB Department of Surgery. A separate database, available only to Dr. Frost, contains patient identifiers, including medical record number, name and surgical pathology number. These experiments will be done by Dr. Frost in her laboratory using commercially available antibodies.

Expected Outcomes (Aim 2)

It is anticipated that decreasing HIF-1α protein will inhibit the bioenergetic response to hypoxia in all breast cancer cells and stem cells which exhibit this phenomenon. If the effects of HIF-1α are transcriptional, then silencing of the transcriptional partner HIF-1β will abrogate the bioenergetic response. However, the fact that the bioenergetic response to hypoxia occurs almost simultaneously with the upregulation of HIF-1α protein (11)(in press, see Appendix 1), suggests that the effects of HIF-1α may be transcriptionally independent. We expect changes in the metabolome, specifically increases in metabolites upstream of the known targets, ACO, IDH, and KGDH (citrate, aconitate, isocitrate) as well as glycolytic intermediates (glucose 6-phosphate, fructose 6-phosphate, fructose 1,6-bisphosphate, pyruvate, and lactate). We do not expect changes in the levels of metabolites downstream of KGDH (succinate, fumarate, and malate) since these metabolites can be provided by other anapleurotic biochemical pathways which feed into the Krebs cycle. We hypothesize that the changes in HIF-1α caused by MTEs are due to inhibition of specific Krebs cycle enzymes, particularly KGDH. This inhibition is expected to result in increased α-ketoglutarate which is required for HIF-1α degradation. For this reason, we expect that silencing of the DLST subunit of KGDH will provide the mechanism by which MTEs decrease HIF-1α.

The subaim involving the tissue microarray is admittedly exploratory, but will likely yield important information regarding the expression of proteins involved in MTE action and hypoxic responses in human breast cancers. We expect that the most aggressive cancer phenotypes will exhibit higher expression of KGDH (as determined by the DLST subunit), and HIF-1α. It is also likely that other subunits of the Krebs cycle are increased in order to dispose of pyruvate and increase glycolytic flux (and thereby provide biosynthetic precursors for proliferation), and also to prevent accumulation of α-ketoglutarate (and thereby stabilize HIF-1α protein and allow metabolic reprogramming).

Alternative Strategies (Aim 2)

It is possible that decreases in HIF-1α protein in response to MTEs is mediated by a pathway other than the prolyl hydroxylase/ubiquitination pathway. Alternative pathways for HIF-1α decreases include decreased HIF-1α mRNA levels, increased degradation by another proteolytic pathway, and/or post-translational modification of HIF-1α protein resulting in epitope masking. In the event that pVHL or prolyl hydroxylase silencing does not prevent the decreased HIF-1α protein in response to MTEs, these alternatives will be explored using a systematic process of elimination. It is also possible that the known targets of MTEs are not responsible for the anti-cancer effects. In this case, we will identify the target of MTEs using a proteomics approach. The PI is experienced in proteomic methods, particularly those involving the detection and identification of post-translationally modified proteins (1, 2, 7-10, 12, 20-34).

Hypothesis 3. MTEs Will Inhibit Tumorigenesis and Chemosensitize Breast Cancer Cells and Stem Cells in In Vivo Models of Tumorigenesis.

Aim 3. To Determine the Efficacy of MTEs in In Vivo Models of Breast Cancer Tumorigenesis In Aim 3, SCID mice will be used to test the bioavailability and efficacy of MTEs against tumor formation alone and in combination with doxorubicin and Abraxane. This aim will determine the conditions for preclinical application of MTEs in breast cancer treatment.

Justification and Feasibility (Aim 32

Mitochondrially-targeted compounds based on the TPP targeting moiety have been used extensively in preclinical models (19, 35) and have recently been tested in human clinical trials (35-37). For example, mitochondrially-targeted coenzyme Q (mitoQ) has been investigated in phase I clinical trials against Parkinson's Disease (PD) (37). Though mitoQ was not found to be effective in PD, it was determined that mitoQ was well tolerated, orally bioavailable, and had very few side effects. These studies have led to an increased interest in the development of mitochondrial drugs for a wide range of pathologies. However, there have been no reports of mitochondrially-targeted electrophilic compounds being tested in preclinical or human studies. Thus, this project represents the first exploration into this area. Because MTEs form covalent adducts with proteins, it is not expected that an oral route of administration will be optimal, since the compounds will need to pass through the gut and liver prior to entering the bloodstream where they may be metabolized. For this reason, i.p. administration will be tested first in order to maximize the drug which enters the bloodstream and tissues adjacent to the mammary fat pads.

It has been previously demonstrated that the monoclonal antibody TRA-8 anti-DR5 and synergizes with the chemotherapeutics doxorubicin or Abraxane to prevent tumorigenesis in orthotopic xenograft models of triple-negative breast cancer cells and stem cells (14, 16).

Research Design (Aim 3)

In these studies, the mouse xenograft models in which human breast cancer cell lines are transplanted to severe combined immunodeficiency mice (SCID) will be used. Tumor growth will be monitored twice weekly by measuring tumor diameter in the two largest dimensions with calipers. Mean tumor size will be calculated from the product of individual tumor diameters and reported relative to tumor size at the start of treatments. Tumor growth, tumor doubling time (TDT), and tumor regression rates will be determined. All studies will be conducted in accordance with the University of Alabama at Birmingham Institutional Animal Care and Use Committee regulations. Mice will be examined daily for physical and behavioral changes and weighed twice weekly to assess toxicity of treatments. Tumor growth will be monitored until the mean tumor size for each group at least doubles in size or until the study is terminated. To accomplish our experimental goals will require n=10 animals for each group, the minimum number predicted to demonstrate a statistical difference based on predicted variability of tumor growth. Analysis of variance (repeated measures ANOVA for repeated measurement over time) will be used to determine if there is a significant difference between groups with error α-0.05.

Subaim 3.1. MTE-Treated Cells (Bioavailability Independent Treatment) in SCID Mice Followed by Chemotherapy:

The experiments in this subaim will determine whether in vitro treatment of cells sensitizes cells to a typical chemotherapeutic regimen using doxorubicin or Abraxane. Breast cancer cells will be selected from Aims 1 and 2, but will be expected to include at least 2 triple-negative breast cancer cell lines and 1 stem cell subpopulation from each of these lines (4 subtypes total). One MTE will be selected based on the ability to inhibit bioenergetic adaptation to hypoxia, chemosensitization, and inhibition of malignant features determined in Aim 1. Cell treatments will include: vehicle alone (veh=EtOH for cell experiments), MTE in EtOH, or a nonelectrophilic analog of the MTE (MT-ne) at 37° C. in 0.5% serum containing medium. The time of treatment will be determined from the results of Aim 1, but is anticipated to be 4 h. Untreated and treated cells ($4 \times 10^6$) will be implanted in a 1:1 mixture with Matrigel into the mammary fat pad. Mice will be treated with doxorubicin (6 mg/kg) or Abraxane (20 mg/kg) by i.v. injection on days 15, 19, and 23. Chemotherapy will be initiated 14 days after implantation when tumors are 5-7 mm in diameter, in applicable groups. Treatment groups in this subaim will include:

| (Total = 90 mice × 4 cell lines = 360 mice) | | |
| --- | --- | --- |
| Group 3.1a | veh only | no chemo |
| Group 3.1b | veh only | DOX |
| Group 3.1c | veh only | Abraxane |
| Group 3.1d | MTE | no chemo |
| Group 3.1e | MTE | DOX |
| Group 3.1f | MTE | Abraxane |
| Group 3.1g | MT-ne | no chemo |

| (Total = 90 mice × 4 cell lines = 360 mice) | | |
|---|---|---|
| Group 3.1h | MT-ne | DOX |
| Group 3.1i | MT-ne | Abraxane | chemotherapy groups, doxorubicin (6 mg/kg for normal dose or 3 mg/kg for low dose) or Abraxane (20 mg/kg for normal dose, or 10 mg/kg for low dose) will be given by i.v. injection on days 15, 19, and 23. The effects on tumor growth, mean tumor size, tumor doubling time (TDT), and tumor regression rates will be determined. An additional experiment is anticipated in order to determine whether additional doses of MTE will be needed.

| (Total = 160 mice × 1 cell line × 2 experiments = 320) | | | |
|---|---|---|---|
| Group 3.3a | cells only (no treatment) | | |
| Group 3.3b | MTE | dose 1 | ⎫ |
| Group 3.3c | MTE | dose 2 | ⎬ no chemo |
| Group 3.3d | MTE | dose 3 | ⎭ |
| Group 3.3e | MTE | dose 1 | ⎫ |
| Group 3.3f | MTE | dose 2 | ⎬ DOX dose 1 (6 mg/kg "normal dose") |
| Group 3.3g | MTE | dose 3 | ⎭ |
| Group 3.3h | MTE | dose 1 | ⎫ |
| Group 3.3i | MTE | dose 2 | ⎬ DOX dose 2 (3 mg/kg "low dose") |
| Group 3.3j | MTE | dose 3 | ⎭ |
| Group 3.3k | MTE | dose 1 | ⎫ |
| Group 3.3l | MTE | dose 2 | ⎬ Abraxane dose 1 (20 mg/kg "normal dose") |
| Group 3.3m | MTE | dose 3 | ⎭ |
| Group 3.3n | MTE | dose 1 | ⎫ |
| Group 3.3o | MTE | dose 2 | ⎬ Abraxane dose 2 (10 mg/kg "low dose") |
| Group 3.3p | MTE | dose 3 | ⎭ |

Subaim 3.2. Mouse Only-Biodistribution by i.p. Injection (Bioavailability Study):

Experiments in this subaim will determine tissue distribution of MTE administered by i.p. injection, and biodistribution will be determined by Western blot analysis for adducts in various tissues. Cells ($4 \times 10^6$) will be implanted in a 1:1 mixture with Matrigel into the mammary fat pad and tumors allowed to develop for 14 days. Mice will be injected i.p. with 3 doses of MTE. Doses of MTE will include a single bolus i.p. injection of 0 (veh), 500, 750, and 1000 nmol MTE/mouse. These values were chosen based on the previously reported daily tolerance of mitoQ by i.p. injection in other studies (38, 39). In that study, no toxicity was observed for mitoQ up to 750 nmol mitoQ/mouse. Veh for animal studies will be DMSO. After 24 h, brain, heart, liver, spleen, and tumors will be harvested, homogenized and analyzed by Western blot using an antibody raised against the TPP moiety. The amount of protein adducts per μg tissue homogenate will be quantified and expressed as a ratio versus tumor (normalized to 1).

| (Total = 40 mice) | |
|---|---|
| Group 3.2a | veh alone |
| Group 3.2b | 500 nmol MTE |
| Group 3.2c | 750 nmol MTE |
| Group 3.2d | 1000 nmol MTE |

Subaim 3.3. Chemosensitization and Dose Study with MTE and Chemotherapy:

In this subaim, one breast cancer cell line will be selected to determine the ability of an MTE to sensitize the cells to chemotherapeutics. Cells ($4 \times 10^6$) will be implanted in a 1:1 mixture with Matrigel into the mammary fat pad and tumors will be allowed to progress for 14 days. On Day 14, mice will be treated by i.p. injection of single bolus doses containing different amounts of MTE. One day later, (Day 14) mice will be treated with chemotherapy or no treatment. For Subaim 3.4. Chemosensitization by MTE in Other Breast Cancer Cell Lines:

Experiments in Subaim 3.3 will determine whether MTEs sensitize existing tumors to doxorubicin and/or Abraxane in one breast cancer cell line, and should provide the optimal dose of MTE. In this subaim, experiments will confirm the key results in Subaim 3.3 in at least one additional breast cancer cell line, and with stem cells derived from each of these lines. The cell line tested in Subaim 3.3 will also be included in order to replicate the findings in an independent experiment. Mice will be treated with MTE by i.p. injection, and/or chemotherapy (doxorubicin 6 or 3 mg/kg or Abraxane 20 or 10 mg/kg) by i.v. injection on days 15, 19, and 23. Chemotherapy will be initiated 14 days after implantation when tumors are 5-7 mm in diameter, in applicable groups.

| (Total = 100 mice × 4 cell lines = 400) | | |
|---|---|---|
| Group 3.4a | veh | no chemo |
| Group 3.4b | veh | DOX "normal dose" |
| Group 3.4c | veh | DOX "low dose" |
| Group 3.4d | veh | Abraxane "normal dose" |
| Group 3.4e | veh | Abraxane "low dose" |
| Group 3.4f | MTE | no chemo |
| Group 3.4g | MTE | DOX "normal dose" |
| Group 3.4h | MTE | DOX "low dose" |
| Group 3.4i | MTE | Abraxane "normal dose" |
| Group 3.4j | MTE | Abraxane "low dose" |

Expected Outcomes (Aim 3)

It is expected that an MTE will sensitize cells to a second hit by either doxorubicin or Abraxane when cells are treated ex vivo, because the delivery of the MTE is readily accomplished using the culture media conditions we have established. It is also expected that MTEs will enter the bloodstream after i.p. injection where they will be delivered to the tumor. Highly metabolic tumor cells should accumulate MTEs in a manner which is analogous to the accumulation of glucose. Therefore, it is anticipated that tumors will have the highest amount of MTE protein adducts compared with other tissues. For the chemosensitization experiments, MTE treatment is likely to decrease the amount of either doxorubicin or Abraxane necessary to cause a significant reduction in tumor growth parameters. Successful accomplishment of this aim is expected to provide proof of concept that MTEs can be used to increase the efficacy of existing chemotherapeutics.

Alternative Strategies (Aim 3)

In these experiments, EtOH will be used a vehicle for MTEs in studies where breast cancer cells and stem cells are treated ex vivo. Since the EtOH is diluted in medium in vitro, we have found it does not exhibit cellular toxicity or otherwise affect the endpoint assays. However, EtOH cannot be injected into mice, therefore, in experiments where MTEs are injected i.p., we will use DMSO as a vehicle. If DMSO causes local irritation, we will use saline instead, provided that the selected MTEs have sufficient solubility. It is also possible that MTEs themselves may cause local adverse reactions when injected i.p. directly into mice. Therefore, during the course of these studies, it may become necessary to adjust dosing schedules to accommodate lower doses of MTEs, or as a last resort, to deliver MTEs via minipumps or other routes of administration (e.g. i.v., topical, intratumor injection, etc.).

It is important to note that because MTEs have never been used in vivo, it is not known whether an MTE injected i.p. will effectively be transported to the tumor site. Since MTEs may bind to proteins adjacent to the injection site, it may become necessary to use an MTE which has lower reactivity (designed in Aim 1.1) for the in vivo experiments. We have previously shown in cell culture model systems that electrophile-protein adducts accumulate over time and may persist up to days (29). Therefore multiple injections of an MTE with lower reactivity may decrease the formation of proteins adducts near the site of injection, while allowing time for diffusion into the bloodstream and into tumor cells before protein adduct formation occurs. The experiments in Subaim 3.2 are designed to determine the distribution of MTE in distal tissues after i.p. injection.

While there is a remote possibility that the MTE chosen will exhibit overt toxicity to the animal, this is not expected based on previous studies using similar nonelectrophilic compounds, and we have chosen electrophiles of relatively low reactivity in order to allow time for diffusion and to prevent nonspecific reactions. We are also able to optimize the design of the electrophiles in the event that the MTE is toxic. It is also possible that MTEs will be metabolized by endogenous detoxification pathways within the animal. This is not likely since there are no functional groups present on the compounds which would allow conjugation by phase I enzymes. Nevertheless, protein adduct formation will be monitored in Subaim 3.2 and alternate MTEs will be chosen or designed/synthesized if necessary. We have the ability to synthesize radiolabeled analogs of an MTE which can be used in whole animal imaging, and this may provide a more sensitive and comprehensive view of the distribution of MTE within the animal as an alternative strategy.

Statistical Analysis

Experiment will be designed in consultation with the CCC Biostatistics and Bioinformatics Shared Facility. In vitro experiments in Aims-1 and -2 will be performed in triplicate and repeated in at least two independent experiments. One-way analysis of variance (ANOVA) will be used to determine whether differences between different groups are significant. Significance also will be analyzed by a 2-tailed t-test with significance defined as $p<0.05$.

References:
1. Diers, A. R., Dranka, B. P., Ricart, K. C., Oh, J. Y., Johnson, M. S., Zhou, F., Pallero, M. A., Bodenstine, T. M., Murphy-Ullrich, J. E., Welch, D. R., and Landar, A. (2010) Modulation of mammary cancer cell migration by 15-deoxy-delta(12,14)-prostaglandin J(2): implications for anti-metastatic therapy. Biochem J 430, 69-78, 2963584 http://www.ncbi.nlm.nih.gov/pubmed/20536428
2. Diers, A. R., Higdon, A. N., Ricart, K. C., Johnson, M. S., Agarwal, A., Kalyanaraman, B., Landar, A., and Darley-Usmar, V. M. (2010) Mitochondrial targeting of the electrophilic lipid 15-deoxy-Delta12,14-prostaglandin J2 increases apoptotic efficacy via redox cell signalling mechanisms. Biochem J 426, 31-41, 3079364 http://www.ncbi.nlm.nih.gov/pubmed/19916962
3. Murphy, M. P. (2008) Targeting lipophilic cations to mitochondria. Biochim Biophys Acta 1777, 1028-1031, http://www.ncbi.nlm.nih.gov/pubmed/18439417
4. Ross, M. F., Da Ros, T., Blaikie, F. H., Prime, T. A., Porteous, C. M., Severina, I I, Skulachev, V. P., Kjaergaard, H. G., Smith, R. A., and Murphy, M. P. (2006) Accumulation of lipophilic dications by mitochondria and cells. Biochem J 400, 199-208, 1635440 http://www.ncbi.nlm.nih.gov/pubmed/16948637
5. Ross, M. F., Prime, T. A., Abakumova, I., James, A. M., Porteous, C. M., Smith, R. A., and Murphy, M. P. (2008) Rapid and extensive uptake and activation of hydrophobic triphenylphosphonium cations within cells. Biochem J 411, 633-645, http://www.ncbi.nlm.nih.gov/pubmed/18294140
6. Li, Z., Lopez, M., Hardy, M., McAllister, D. M., Kalyanaraman, B., and Zhao, M. (2009) A (99m)Tc-labeled triphenylphosphonium derivative for the early detection of breast tumors. Cancer Biother Radiopharm 24, 579-587, 2883499 http://www.ncbi.nlm.nih.gov/pubmed/19877888
7. Dranka, B. P., Benavides, G. A., Diers, A. R., Giordano, S., Zelickson, B. R., Reily, C., Zou, L., Chatham, J. C., Hill, B. G., Zhang, J., Landar, A., and Darley-Usmar, V. M. (2011) Assessing bioenergetic function in response to oxidative stress by metabolic profiling. Free Radic Biol Med 51, 1621-1635, http://www.ncbi.nlm.nih.gov/pubmed/21872656
8. Higdon, A., Diers, A. R., Oh, J. Y., Landar, A., and Darley-Usmar, V. M. (2012) Cell signalling by reactive lipid species: new concepts and molecular mechanisms. Biochem J 442, 453-464, 3286857 http://www.ncbi.nlm.nih.gov/pubmed/22364280
9. Oliva, C. R., Nozell, S. E., Diers, A., McClugage, S. G., 3rd, Sarkaria, J. N., Markert, J. M., Darley-Usmar, V. M., Bailey, S. M., Gillespie, G. Y., Landar, A., and Griguer, C. E. (2010) Acquisition of temozolomide chemoresistance in gliomas leads to remodeling of mitochondrial electron transport chain. J Biol Chem 285, 39759-39767, 3000957 http://www.ncbi.nlm.nih.gov/pubmed/20870728
10. Zelickson, B. R., Benavides, G. A., Johnson, M. S., Chacko, B. K., Venkatraman, A., Landar, A., Betancourt, A. M., Bailey, S. M., and Darley-Usmar, V. M. (2011) Nitric oxide and hypoxia exacerbate alcohol-induced mitochondrial dysfunction in hepatocytes. Biochim Biophys Acta 1807, 1573-1582, 3217123 http://www.ncbi.nlm.nih.gov/pubmed/21971515
11. Diers, A. R., Vayalil, P. K., Oliva, C. R., Griguer, C. E., Darley-Usmar, V., Hurst, D. R., Welch, D. R., Landar, A. (in press) Mitochondrial bioenergetics of metastatic breast cancer cells in response to dynamic changes in oxygen tension: Effects of HIF-1a. *PLoS One*

12. Ricart, K. C., Bolisetty, S., Johnson, M. S., Perez, J., Agarwal, A., Murphy, M. P., and Landar, A. (2009) The permissive role of mitochondria in the induction of haem oxygenase-1 in endothelial cells. *Biochem J* 419, 427-436, 2737281 http://www.ncbi.nlm.nih.gov/pubmed/19161347

13. Marley, K., Mooney, D. T., Clark-Scannell, G., Tong, T. T., Watson, J., Hagen, T. M., Stevens, J. F., and Maier, C. S. (2005) Mass tagging approach for mitochondrial thiol proteins. *J Proteome Res* 4, 1403-1412, http://www.ncbi.nlm.nih.gov/pubmed/16083293

14. Londono-Joshi, A. I., Oliver, P. G., Li, Y., Lee, C. H., Forero-Torres, A., LoBuglio, A. F., and Buchsbaum, D. J. (2012) Basal-like breast cancer stem cells are sensitive to anti-DR5 mediated cytotoxicity. *Breast Cancer Res Treat* 133, 437-445, 3609658 http://www.ncbi.nlm.nih.gov/pubmed/21915634

15. Lin, T. K., Hughes, G., Muratovska, A., Blaikie, F. H., Brookes, P. S., Darley-Usmar, V., Smith, R. A., and Murphy, M. P. (2002) Specific modification of mitochondrial protein thiols in response to oxidative stress: a proteomics approach. *The Journal of biological chemistry* 277, 17048-17056, http://www.ncbi.nlm.nih.gov/pubmed/11861642

16. Oliver, P. G., LoBuglio, A. F., Zhou, T., Forero, A., Kim, H., Zinn, K. R., Zhai, G., Li, Y., Lee, C. H., and Buchsbaum, D. J. (2012) Effect of anti-DR5 and chemotherapy on basal-like breast cancer. *Breast Cancer Res Treat* 133, 417-426, 3613128 http://www.ncbi.nlm.nih.gov/pubmed/21901385

17. Kleinman, H. K., and Jacob, K. (2001) Invasion assays. *Curr Protoc Cell Biol* Chapter 12, Unit 12.12, http://www.ncbi.nlm.nih.gov/pubmed/18228316

18. McGonigle, S., and Shifrin, V. (2008) In vitro assay of angiogenesis: inhibition of capillary tube formation. *Curr Protoc Pharmacol* Chapter 12, Unit12.12, http://www.ncbi.nlm.nih.gov/pubmed/22294219

19. Smith, R. A., Hartley, R. C., and Murphy, M. P. (2011) Mitochondria-targeted small molecule therapeutics and probes. *Antioxid Redox Signal* 15, 3021-3038, http://www.ncbi.nlm.nih.gov/pubmed/21395490

20. Fenster, C. P., Darley-Usmar, V. M., Landar, A. L., Gower, B. A., Weinsier, R. L., Hunter, G. R., and Patel, R. P. (2004) Weight loss and race modulate nitric oxide metabolism in overweight women. *Free Radic Biol Med* 37, 695-702, http://www.ncbi.nlm.nih.gov/pubmed/15288126

21. Venkatraman, A., Landar, A., Davis, A. J., Chamlee, L., Sanderson, T., Kim, H., Page, G., Pompilius, M., Ballinger, S., Darley-Usmar, V., and Bailey, S. M. (2004) Modification of the mitochondrial proteome in response to the stress of ethanol-dependent hepatotoxicity. *The Journal of biological chemistry* 279, 22092-22101, http://www.ncbi.nlm.nih.gov/pubmed/15033988

22. Venkatraman, A., Landar, A., Davis, A. J., Ulasova, E., Page, G., Murphy, M. P., Darley-Usmar, V., and Bailey, S. M. (2004) Oxidative modification of hepatic mitochondria protein thiols: effect of chronic alcohol consumption. *Am J Physiol Gastrointest Liver Physiol* 286, G521-527, http://www.ncbi.nlm.nih.gov/pubmed/14670822

23. Bailey, S. M., Landar, A., and Darley-Usmar, V. (2005) Mitochondrial proteomics in free radical research. *Free Radic Biol Med* 38, 175-188, http://www.ncbi.nlm.nih.gov/pubmed/15607901

24. Bailey, S. M., Robinson, G., Pinner, A., Chamlee, L., Ulasova, E., Pompilius, M., Page, G. P., Chhieng, D., Jhala, N., Landar, A., Kharbanda, K. K., Ballinger, S., and Darley-Usmar, V. (2006) S-adenosylmethionine prevents chronic alcohol-induced mitochondrial dysfunction in the rat liver. *Am J Physiol Gastrointest Liver Physiol* 291, G857-867, http://www.ncbi.nlm.nih.gov/pubmed/16825707

25. Landar, A., Oh, J. Y., Giles, N. M., Isom, A., Kirk, M., Barnes, S., and Darley-Usmar, V. M. (2006) A sensitive method for the quantitative measurement of protein thiol modification in response to oxidative stress. *Free Radic Biol Med* 40, 459-468, http://www.ncbi.nlm.nih.gov/pubmed/16443161

26. Landar, A., Shiva, S., Levonen, A. L., Oh, J. Y., Zaragoza, C., Johnson, M. S., and Darley-Usmar, V. M. (2006) Induction of the permeability transition and cytochrome c release by 15-deoxy-Delta12,14-prostaglandin J2 in mitochondria. *Biochem J* 394, 185-195, 1386016 http://www.ncbi.nlm.nih.gov/pubmed/16268779

27. Oh, J., Johnson, M. S., and Landar, A. (2007) Methods for determining the modification of protein thiols by reactive lipids. *Methods Cell Biol* 80, 417-434, http://www.ncbi.nlm.nih.gov/pubmed/17445707

28. Bailey, S. M., Andringa, K. K., Landar, A., and Darley-Usmar, V. M. (2008) Proteomic approaches to identify and characterize alterations to the mitochondrial proteome in alcoholic liver disease. *Methods Mol Biol* 447, 369-380, 2935618 http://www.ncbi.nlm.nih.gov/pubmed/18369930

29. Oh, J. Y., Giles, N., Landar, A., and Darley-Usmar, V. (2008) Accumulation of 15-deoxy-delta(12,14)-prostaglandin J2 adduct formation with Keap1 over time: effects on potency for intracellular antioxidant defence induction. *Biochem J* 411, 297-306, 2683789 http://www.ncbi.nlm.nih.gov/pubmed/18237271

30. Higdon, A. N., Dranka, B. P., Hill, B. G., Oh, J. Y., Johnson, M. S., Landar, A., and Darley-Usmar, V. M. (2009) Methods for imaging and detecting modification of proteins by reactive lipid species. *Free Radic Biol Med* 47, 201-212, 2727357 http://www.ncbi.nlm.nih.gov/pubmed/19446632

31. Hill, B. G., Reily, C., Oh, J. Y., Johnson, M. S., and Landar, A. (2009) Methods for the determination and quantification of the reactive thiol proteome. *Free Radic Biol Med* 47, 675-683, 2759107 http://www.ncbi.nlm.nih.gov/pubmed/19527783

32. Andringa, K. K., King, A. L., Eccleston, H. B., Mantena, S. K., Landar, A., Jhala, N. C., Dickinson, D. A., Squadrito, G. L., and Bailey, S. M. (2010) Analysis of the liver mitochondrial proteome in response to ethanol and S-adenosylmethionine treatments: novel molecular targets of disease and hepatoprotection. *Am J Physiol Gastrointest Liver Physiol* 298, G732-745, 2867419 http://www.ncbi.nlm.nih.gov/pubmed/20150243

33. Charles, R. L., Burgoyne, J. R., Mayr, M., Weldon, S. M., Hubner, N., Dong, H., Morisseau, C., Hammock, B. D., Landar, A., and Eaton, P. (2011) Redox regulation of soluble epoxide hydrolase by 15-deoxy-delta-prostaglandin J2 controls coronary hypoxic vasodilation. *Circ Res* 108, 324-334, 3259859 http://www.ncbi.nlm.nih.gov/pubmed/21164107

34. Wall, S. B., Oh, J. Y., Diers, A. R., and Landar, A. (2012) Oxidative modification of proteins: an emerging mechanism of cell signaling. Front Physiol 3, 369, 3442266 http://www.ncbi.nlm.nih.gov/pubmed/23049513

35. Smith, R. A., and Murphy, M. P. (2010) Animal and human studies with the mitochondria-targeted antioxidant MitoQ. *Ann N Y Acad Sci* 1201, 96-103, http://www.ncbi.nlm.nih.gov/pubmed/20649545
36. Gane, E. J., Weilert, F., Orr, D. W., Keogh, G. F., Gibson, M., Lockhart, M. M., Frampton, C. M., Taylor, K. M., Smith, R. A., and Murphy, M. P. (2010) The mitochondria-targeted anti-oxidant mitoquinone decreases liver damage in a phase II study of hepatitis C patients. *Liver Int* 30, 1019-1026, http://www.ncbi.nlm.nih.gov/pubmed/20492507
37. Snow, B. J., Rolfe, F. L., Lockhart, M. M., Frampton, C. M., O'Sullivan, J. D., Fung, V., Smith, R. A., Murphy, M. P., and Taylor, K. M. (2010) A double-blind, placebo-controlled study to assess the mitochondria-targeted antioxidant MitoQ as a disease-modifying therapy in Parkinson's disease. *Mov Disord* 25, 1670-1674, http://www.ncbi.nlm.nih.gov/pubmed/20568096
38. Smith, R. A., and Murphy, M. P. (2011) Mitochondria-targeted antioxidants as therapies. *Discov Med* 11, 106-114, http://www.ncbi.nlm.nih.gov/pubmed/21356165
39. Smith, R. A., Porteous, C. M., Gane, A. M., and Murphy, M. P. (2003) Delivery of bioactive molecules to mitochondria in vivo. *Proc Natl Acad Sci USA* 100, 5407-5412, 154358 http://www.ncbi.nlm.nih.gov/pubmed/12697897

B. Structure of IBTP and Analogs Thereof

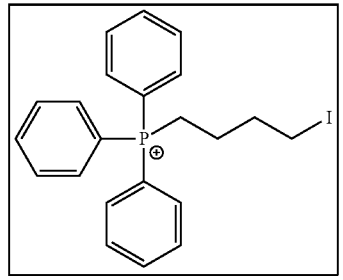 [SMILES: ICCCC[P+](c1ccccc1)(c1ccccc1)c1ccccc1]

FIG. 1. The structure of IBTP. IBTP consists of three phenyl groups, a phosphonium cation, and an electrophilic iodo group linked by a 4 carbon alkyl chain. The delocalized nature of the cation and the high lipophilicity allow rapid entry into the mitochondrion and accumulation based on mitochondrial membrane potential. Once the molecule is localized to the mitochondrion, it reacts with specific protein cysteines residues and forms a covalent adducts.

The overall objective of this application is to rationally modulate the key chemical features of IBTP in order to improve its anti-adhesion activity. The experiments in this proposal are focused on developing and testing a series of IBTP analogs as mitochondrially-targeted electrophiles. This study will give important insights into the potential for novel mitochondrially-targeted redox therapeutics in cancer. The central hypothesis of this project is that reactivity and alkyl chain length determine the efficacy of mitochondrially-targeted electrophiles against cancer cell adhesion, an important property in cancer cell metastasis. The hypothesis will be tested by the following specific aims:

Specific Aim #1:
Determine the effects of chain length on efficacy of iodo triphenyl phosphonium compounds on the adhesion and migration of metastatic, tumorigenic breast adenocarcinoma cells (MDA-MB 231).

In this aim, the alkyl chain length of iodo triphenyl phosphonium will be varied and compounds containing alkyl chains with 2, 4, 6, 8, and 10 carbons will be chemically synthesized, purified, and then characterized in a breast cancer cell model.

Specific Aim #2:
Determine the effects of leaving group on efficacy of electrophilic triphenyl phosphonium compounds on the adhesion and migration of metastatic, tumorigenic breast adenocarcinoma cells (MDA-MB 231).

In this aim, IBTP analogs containing 4-carbon alkyl chain will be synthesized with more or less favorable leaving groups such as Br, Cl or mesylate,—thus making these compounds more or less reactive electrophiles. Compounds will be purified, and then characterized in a breast cancer cell model.

It is expected that Aim 1 will characterize the optimal chain length and Aim 2 will determine the optimal reactivity of the electrophilic moiety for inhibition of cancer cell adhesion. Overall, these experiments will identify the most efficacious reagent against cancer cell adhesion, which can be studied further in animal models of breast cancer metastasis.

Approach

These studies are centered on the observation that IBTP inhibits breast cancer cell adhesion. IBTP has been shown to accumulate in the mitochondrial matrix 200-500 fold over the concentration added to the extracellular milieu, and covalently modifies specific protein cysteine residues by addition of a butyl triphenylphosphonium adduct to the protein. Our laboratory has experience with IBTP. It is important to note that IBTP is moderately reactive and will only form adducts with cysteine residues which are deprotonated at physiological pH (which are found in a small subset of protein thiols. Also, the equilibration dynamics of mitochondrially targeted compounds has been shown to be dependent on alkyl chain length. Thus, modulating alkyl chain length and reactivity may significantly alter the effects of IBTP on cancer cell adhesion.

Preliminary Data

It has recently been observed that MDA-MB 231 breast cancer cells (one of the most invasive/metastatic cell lines available to study breast carcinoma) treated with 10 μM IBTP for 24 h. failed to reattach to tissue culture plates after scraping, while cells treated with a non-electrophilic analog exhibited no changes in reattachment (FIG. 2). Interestingly, there was no evidence of overt cell death, despite significantly decreased clonogenic survival at 10 μM IBTP (data not shown). These results demonstrate that a mitochondrially-targeted electrophile exhibits activity against a biologically important property of metastatic cells, adhesion. The studies in this proposal will determine whether a more potent analog can be designed which inhibits key properties of metastatic cells in a cell culture model, adhesion, migration, and invasion.

FIG. 2. Two×$10^5$ cells/plate were plated on a 6-well plate, 24 hrs after plating cells were starved in 0.5% FCS containing media for another 24 hrs.

Cells were then treated for another 24 hrs with increasing doses of IBTP or the non-reactive analog butyl-triphenylphosphonium (BTPP) as a control. Cells were scraped and made into single cell suspension. Cells were counted and plated in 100-mm tissue culture plate. After 24 hrs the media is collected, centrifuged and the viable cells were counted using trypan blue.

Research Design (Aim 1)

Specific Aim #1:

Determine the effects of chain length on efficacy of iodo triphenyl phosphonium compounds on the adhesion and migration of metastatic, tumorigenic breast adenocarcinoma cells (MDA-MB 231).

IBTP used in the preliminary studies contains a 4 carbon alkyl chain. In order to evaluate the modulatory effect of alkyl chain length we propose to synthesize four analogs of IBTP containing 2, 6, 8 and 10 carbon alkyl chains. Proposed target molecules (2a-d) and their synthesis are shown in FIG. 3. These four analogs will be synthesized. IBTP used in the preliminary studies was produced following a literature procedure (3). The target compounds will be synthesized following a similar procedure by treating Triphenyl phosphine with 1,2-diiodoethane, 1,6-diiodohexane, 1,8-diiodooctane or 1,10-diiododecane respectively as outlined in FIG. 3. Purity of all of target compounds will be evaluated by $^1$H-NMR, $^{13}$C-NMR and MS and made sure that they meet purity criteria (99.9%) before subjected to biological evaluations.

FIG. 3: Synthesis of Target Compound Class I

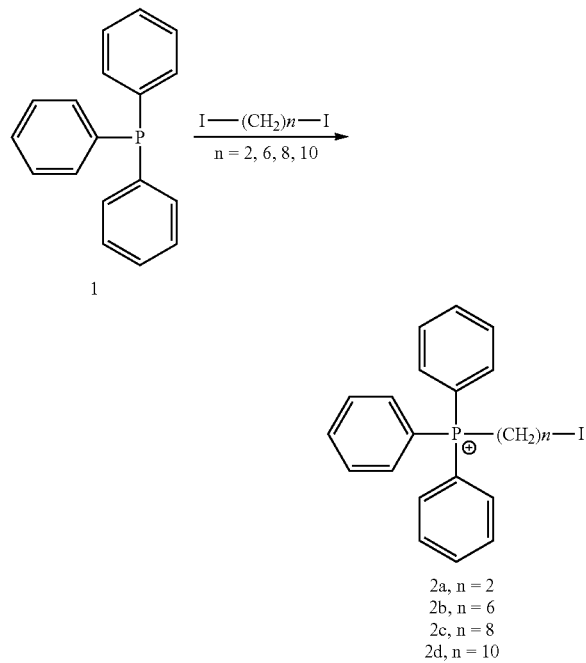

2a, n = 2
2b, n = 6
2c, n = 8
2d, n = 10

Cell adhesion will be determined using a breast cancer cell line (MDA-MB 231). $1.2 \times 10^5$ cells/plate will be plated on a 6-well plate, 24 hrs after plating cells will be starved in 0.5% FCS containing media for another 24 hrs. Cells will then be treated with a dose range of analogs 2a, 2b, 2c, and 2d containing alkyl chains of 2, 6, 8, or 10 carbons at 0-25 mM for another 24 h. Non-electrophilic analogs will be used as controls, and are available commercially. Viability will be determined for each concentration using LDH release assay, and key results confirmed using trypan blue exclusion and caspase cleavage. Non-lethal doses will be used for time course experiments and cells will be treated with a fixed concentration of the analogs for times ranging from 1 h-18 h. Cells will be scraped and made into single cell suspension, then counted and plated in a 100-mm tissue culture plate. After 24 hrs the media will be collected, centrifuged and the viable cells counted using trypan blue.

Cellular migration will be determined using a scratch assay and a matrigel invasion assay. For the scratch assay, cells will be grown to confluence in 6 well plates, and then scratched with the narrow end of a sterile pipette tip. Medium will be immediately changed to remove floating cells and will be replaced with media containing increasing concentrations of IBTP, electrophilic IBTP analogs, non-electrophilic analogs, or vehicle control. The width of the scratch will be measured at four points in each well after initial wounding, and cells will be incubated for 8 h at 37° C. in a $CO_2$-incubator. After 8 h, the scratch width will be measured again, and the ability of the cells to migrate into the cell-free zone (relative motility) will be expressed as the normalized percent change in the width of the scratch after 8 h compared to vehicle control.

For the matrigel invasion assay, six-well plate trans-well inserts with 8-μm pore-size polycarbonate filters (BD Biosciences) will be coated with Matrigel (0.7 mg/ml) in cold serum-free DMEM/F12 medium and will be placed at room temperature for 1 h. The MDA-MB-231 cells ($3 \times 10^5$ cells) will be resuspended in 500 μl serum free media and will be added into the Matrigel-coated transwell inserts. The plate will be incubated for 72 h in the absence or presence of IBTP, electrophilic IBTP analogs, non-electrophilic analogs, or vehicle control. The lower chambers will be filled with 2 nil DMEM/F12 medium supplemented with 5% FBS. After incubation, noninvading cells on the upper surface of the filter will be removed with cotton swabs. Cells that invade through the pores onto the lower side of the filter will be fixed, stained with Geimsa stain, and photographed. The invaded cells will be counted in five fields for each filter under a light microscope at 40× magnification. The invasiveness of the cells will be expressed as the mean number of cells that had invaded to the lower side of the filter. The experiments will be performed in triplicate wells.

All experiments will be performed in triplicate and replicated a minimum of 3 independent times. Statistical analyses will include ANOVA and appropriate post-test analyses in consultation with the Biostatistics Core of the Comprehensive Cancer Center here at UAB. Chain lengths which cause a significant decrease in cell adhesion compared to IBTP will be determined to exhibit increased efficacy for this endpoint.

Alternative Strategies (Aim 1)

We may use large excess of diiodoalkane reagents (7-10 molar equivalents) in this synthesis. With the cellular assays, it is possible that the compounds will exhibit variable efficacy in different cellular endpoints. However, each endpoint is designed to give specific information about adhesion, migration, or invasion into a simulated extracellular matrix. For purposes of choosing a lead compound for further study, compounds which exhibit inhibitory activity in all three endpoints will be chosen for follow-up. It is possible that altering the leaving group will change the uptake of the compounds into the mitochondrion and that one or more analogs may not form protein adducts. In the event, that an analog does not alter any of the cellular endpoints, we will test to determine whether the compounds entered the mitochondrion and formed protein adducts by Western blot analysis of the triphenyl phosphonium group in mitochondrially-enriched cellular fractions. If no adducts are found, then an alternate leaving group will be designed, synthesized and tested. However, this is highly unlikely since numerous groups have been added to the triphenyl phosphonium moiety and all compounds reported have been shown to enter the mitochondrion thus far (4).

Research Design (Aim 2)

Specific Aim #2:

Determine the effects of leaving group on efficacy of electrophilic triphenyl phosphonium compounds on the adhesion and migration of metastatic, tumorigenic breast adenocarcinoma cells (MDA-MB 231).

In this aim, IBTP analog compounds containing 4-carbon alkyl chain and different leaving groups will be synthesized and evaluated. The goal is to modulate the reactivity of the electrophile by changing the leaving group from I in to worse leaving groups such as Cl or Br and better leaving groups such as OMs. Proposed target compounds (3a, 3b and 4c) and their synthesis are outlined in FIG. 4. All analogs will be synthesized. Triphenyl phosphine will be treated with 1-chloro-4-iodobutane to form target compound 3a. Triphenyl phosphine will be treated with 1-bromo-4-iodobutane to form target compound 3b. Triphenyl phosphine will be treated with 4-iodo-1-butanol to form the intermediate compound 3c, which in turn will be treated with methane sulfonyl chloride in the presence of $Et_3N$ to afford the target mesylate compound 4c. Purity of all of target compounds will be evaluated by $^1H$-NMR, $^{13}C$-NMR and MS and made sure that they meet purity criteria (99.9%) before subjected to biological evaluation.

FIG. 4: Synthesis of Target Compound Class II

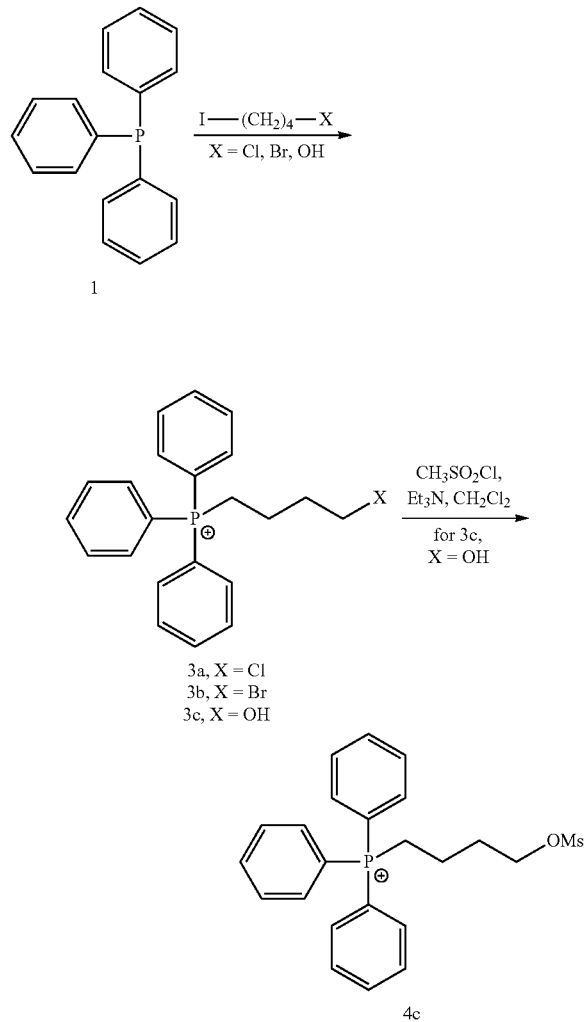

All three target compounds (3a, 3b and 4c) will be then characterized in a breast cancer cell model as described in Aim 1.

Alternative Strategies (Aim 2)

Such compositions resulting from the present invention could be used alone, or in combination with conventional therapies, to significantly increase survival rates/times for patients diagnosed with localized breast cancer and/or prevent/reduce the progression of localized to metastatic breast cancer.

Anticipated Outcomes

Our preliminary data demonstrate that a mitochondrially-targeted electrophile has significant effects by decreasing cancer cell adhesion at concentrations which do not induce cell death. FIG. 2 shows that 10 μM IBTP inhibits the adhesion of approximately 15% of MDA-MB 231 cells after detachment. In order to inhibit the adhesion of a greater number of cells, we could use a higher concentration of IBTP. However, our experience in several cell types suggests that higher concentrations of IBTP, or any mitochondrially-targeted molecule, can be cytotoxic in MDA-MB 231 cells, and also in other cell types. Therefore it is necessary to develop novel drug leads which do not have general toxicity, but specifically target cell. It is anticipated that some of the compounds that will be developed during this project will inhibit the adhesion of a greater number of cells at the same or lower concentrations. In this proposal, we expect that alterations in chain length (Aim 1) will change the time course since more hydrophobic compounds equilibrate more rapidly than shorter chain lengths. We expect that varying the reactivity of the electrophilic functional group (Aim 2) will result in more or less potent compounds which may either increase the anti-metastatic efficacy (more reactive electrophiles), or will decrease toxicity and off-target effects (less reactive electrophiles). Overall, these studies will determine which IBTP analogs can be developed against breast cancer cell metastatic properties, and these analogs can be further studied in in vivo models of metastasis.

REFERENCES

1. Chambers, A. F., Groom, A. C., and MacDonald, I. C. (2002) Dissemination and growth of cancer cells in metastatic sites. *Nat Rev Cancer* 2, 563-572
2. Steeg, P. S. (2006) Tumor metastasis: mechanistic insights and clinical challenges. *Nat Med* 12, 895-904
3. Lin, T. K., Hughes, G., Muratovska, A., Blaikie, F. H., Brookes, P. S., Darley-Usmar, V., Smith, R. A., and Murphy, M. P. (2002) Specific modification of mitochondrial protein thiols in response to oxidative stress: a proteomics approach. *J Biol Chem* 277, 17048-17056
4. Smith, R. A., Hartley, R. C., and Murphy, M. P. (2011) Mitochondria-targeted small molecule therapeutics and probes. *Antioxid Redox Signal* 15, 3021-3038

The foregoing is illustrative of the present invention, and is not to be construed as limiting thereof. The invention is defined by the following claims, with equivalents of the claims to be included therein.

What is claimed is:

1. A method of treating breast cancer, comprising administering to a subject an effective amount of a mitochondrially-targeted electrophilic (MTE) compound having the following structure:

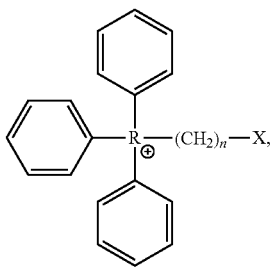

wherein R is an ammonium, sulfonium or phosphonium cation;
n is 1 to 15; and
X is I, Br, Cl or mesylate, with the proviso that the analog is not IBTP.

2. The method of claim 1, wherein the cancer is triple negative.

3. The method of claim 1, wherein the cancer is treatment resistant.

4. The method of claim 1, wherein the MTE compound is radiolabeled.

5. The method of claim 1, wherein the MTE compound is administered in combination with a chemotherapeutic agent.

6. The method of claim 5, wherein the MTE compound is administered prior to, concurrently with, or after administration of the chemotherapeutic agent.

7. A method of reducing breast cancer metastasis, comprising administering to a subject an effective amount of a mitochondrially-targeted electrophilic (MTE) compound having the following structure:

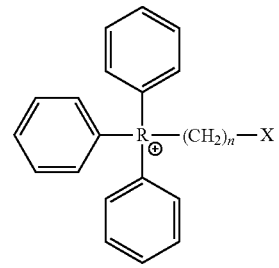

wherein R is an ammonium, sulfonium or phosphonium cation;
n is 1 to 15; and
X is I, Br, Cl or mesylate, with the proviso that the analog is not IBTP.

* * * * *